US008837107B2

(12) United States Patent
Hinz et al.

(10) Patent No.: US 8,837,107 B2
(45) Date of Patent: Sep. 16, 2014

(54) SYSTEMS AND METHODS FOR WEAPONRY WITH LOWER TIP CURRENT ELECTRODE

(71) Applicant: TASER International, Inc., Scottsdale, AZ (US)

(72) Inventors: Andrew F. Hinz, Mesa, AZ (US); Patrick W. Smith, Scottsdale, AZ (US); Magne H. Nerheim, Paradise Valley, AZ (US)

(73) Assignee: TASER International, Inc., Scottsdale, AZ (US)

( * ) Notice: Subject to any disclaimer, the term of this patent is extended or adjusted under 35 U.S.C. 154(b) by 0 days.

(21) Appl. No.: 13/749,478

(22) Filed: Jan. 24, 2013

(65) Prior Publication Data

US 2014/0111902 A1 Apr. 24, 2014

Related U.S. Application Data

(63) Continuation of application No. 12/833,854, filed on Jul. 9, 2010, now Pat. No. 8,441,771.

(60) Provisional application No. 61/228,115, filed on Jul. 23, 2009.

(51) Int. Cl.
*C07C 11/24* (2006.01)

(52) U.S. Cl.
USPC .......................................... 361/232; 42/1.08

(58) Field of Classification Search
USPC .......................... 361/232; 42/1.08; 102/502
See application file for complete search history.

(56) References Cited

U.S. PATENT DOCUMENTS

| | | | | |
|---|---|---|---|---|
| 3,771,249 | A * | 11/1973 | Johnson et al. | 43/6 |
| 5,698,815 | A * | 12/1997 | Ragner | 102/502 |
| 2006/0086032 | A1 | 4/2006 | Valencic et al. | |
| 2010/0089273 | A1* | 4/2010 | Kroll et al. | 102/502 |

* cited by examiner

*Primary Examiner* — Danny Nguyen

(74) *Attorney, Agent, or Firm* — William R. Bachand; Lawrence Letham

(57) ABSTRACT

An electronic weapon has an installed deployment unit, from which at least one tethered electrode is launched, provides a stimulus current through a target to inhibit locomotion by the target. The wire tether, also called a filament, conducts the stimulus current. The one or more electrodes, according to various aspects of the present invention, perform one or more of the following functions in any combination: binding the filament to the electrode, deploying the filament from the deployment unit, coupling the electrode to the target, and distributing a current density with respect to a volume of target tissue. An electrode may include conductive material and insulative material. Relatively high electric field flux density at a tip of the electrode may be reduced or avoided by practice of the invention.

15 Claims, 11 Drawing Sheets

SYSTEMS AND METHODS FOR WEAPONRY WITH LOWER TIP CURRENT ELECTRODE

CROSS-REFERENCE TO RELATED APPLICATIONS

This application is a continuation of and claims priority under 35 U.S.C. §120 from U.S. patent application Ser. No. 12/833,854 filed Jul. 9, 2010 by Hinz which claims the benefit under 35 U.S.C. §119(e) of U.S. Provisional Patent Application Ser. No. 61/228,115 filed Jul. 23, 2009 by Hinz.

FIELD OF THE INVENTION

Embodiments of the present invention relate to electronic weaponry, deployment units, and electrodes used in deployment units for electronic weaponry, and to methods of providing a current through a human or animal target via at least one electrode having a current spreading capability.

BACKGROUND OF THE INVENTION

Conventional electronic weapons launch one or more electrodes toward a human or animal target to deliver a stimulus signal through the target to inhibit locomotion by the target. A thin wire couples a signal generator in the electronic weapon to a launched electrode positioned in or near the target. The signal generator provides the stimulus signal through the target via the filament(s), the one or more electrodes, and a return path to complete a closed circuit. The return path may be through earth and/or through a second filament and electrode. Conventional electrodes are made of conductive materials and have a sharp barbed tip to acquire and remain in a position in or near a target (e.g., lodge in clothing, skin). Consequently, relatively high field strengths and current densities occur at the electrode tip.

A conventional electrode is assembled by inserting a sharpened shaft into an axial hole in a forward face of a cylindrical body, crimping the body to retain the shaft, threading a filament through a second axial hole in a rearward face of the body and into an open portion of the body, tying a knot in the filament, and pulling the knot into the open portion of the body. Electronic weapons may benefit from an electrode that costs less to manufacture, reduces labor required to couple the electrode to the filament, and reduces damage to the filament during assembly.

BRIEF DESCRIPTION OF THE DRAWING

Embodiments of the present invention are described with reference to the drawing, wherein like designations denote like elements, and.

DETAILED DESCRIPTION OF THE PREFERRED EMBODIMENTS

Figure 1A:
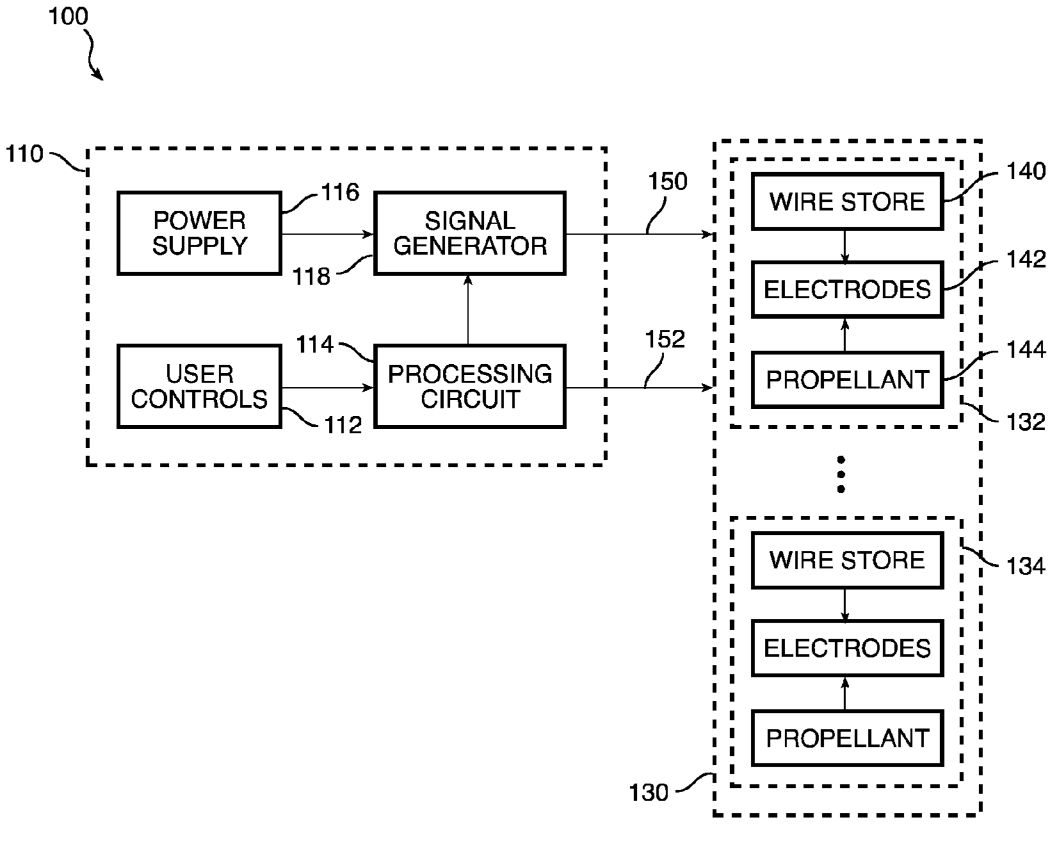
FIG. 1A is a functional block diagram of an electronic weapon according to various aspects of the present invention.

An electronic weapon, according to various aspects of the present invention, delivers a current through a human or animal target to interfere with locomotion by the target. An important class of electronic weapons launch at least one wire-tethered electrode, also called a dart or a probe, toward a target to position the electrode in or near target tissue. A respective filament (e.g., wire with or without insulation) extends from the electronic weapon to each electrode at the target. One or more electrodes may form a circuit through a target. The circuit conducts the stimulus signal. The circuit may include a return path as discussed above. The electronic weapon provides a stimulus signal (e.g., current, pulses of current) through, inter alia, the filament, the electrode, and the target to interfere with locomotion by the target. Interference includes causing involuntary contraction of skeletal muscles to halt voluntary locomotion by the target and/or causing pain to the target to motivate the target to voluntarily stop moving.

An electronic weapon, according to various aspects of the present invention, may include a launch device and one or more field replaceable deployment units. Each deployment unit may include expendable (e.g., single use) components (e.g., tether wires, electrodes, propellant). Herein, the tether is interchangeably called a wire, a tether wire, and a filament. A wire-tethered electrode is an assembly of a filament and an electrode at least mechanically coupled to one end of the filament. The other end of the filament is at least mechanically coupled to the deployment unit and/or the launch device (e.g., one end fixed within the deployment unit), generally until the deployment unit is removed from the electronic weapon. As discussed below, mechanical coupling may facilitate electrical coupling of the launch device and the target prior to and/or during operation of the electronic weapon.

A launch device of an electronic weapon launches at least one wire-tethered electrode of the electronic weapon toward a target. As the electrode travels toward the target, the electrode deploys (e.g., pulls) a length of filament from a wire store. The filament trails the electrode. After launch, the filament spans (e.g., extends, bridges, stretches) a distance from the launch device to the electrode generally positioned in or near a target.

Electronic weapons that use wire-tethered electrodes, according to various aspects of the present invention, include handheld devices, apparatus fixed to buildings or vehicles, and stand-alone stations. Hand-held devices may be used in law enforcement, for example, deployed by an officer to take custody of a target. Apparatus fixed to buildings or vehicles may be used at security checkpoints or borders, for example, to manually or automatically acquire, track, and/or deploy electrodes to stop intruders. Stand-alone stations may be set up for area denial, for example, as used by military operations. Conventional electronic weapons such as the model X26 electronic control device and Shockwave™ area denial unit marketed by TASER International, Inc. may be modified to implement the teachings of the present invention by replacing the conventional deployment units with deployment units having electrodes as discussed herein.

An electrode, according to various aspects of the present invention, provides a mass for launching toward a target. The intrinsic mass of an electrode includes a mass that is sufficient to fly, under force of a propellant, from a launch device to a target. The mass of the electrode includes a mass that is sufficient to deploy (e.g., pull, uncoil, unravel, draw) a filament from a wire store. The mass of the electrode is sufficient to deploy a filament behind the electrode while the electrode flies toward a target. The mass of the electrode deploys the filament from the wire store and behind the electrode in such a manner that the filament spans a distance between the launch device and the electrode positioned at a target. The mass of an electrode is generally insufficient to cause serious blunt impact trauma to a target. In one implementation, the mass of an electrode is in the range of 2.0 to 3.0 grams, preferably about 2.8 grams.

An electrode provides a surface area for receiving a propelling force to propel the electrode away from a launch device and toward a target. Movement of the electrode away from the launch device is limited by aerodynamic drag and resistance force (e.g., tension in the filament) that resists deploying a filament from a wire store and pulling the filament behind the electrode in flight toward a target.

A forward portion of an electrode may be oriented toward a target prior to launch. Upon launch and/or during flight from the launch device toward the target, the forward portion of the electrode orients toward the target. An electrode has an aerodynamic form for maintaining the forward portion of the electrode oriented toward a target. The aerodynamic form of an electrode provides suitable accuracy for hitting the target.

An electrode includes a shape for receiving a propelling force to propel the electrode toward a target. A shape of an electrode may correspond to a shape of a portion of the launch device or deployment unit that provides a propelling force to propel the electrode. For example, a cylindrical electrode may be propelled from a cylindrical tube of a deployment unit. During a launch of an electrode by expanding gas, the electrode may seal the tube with the body of the electrode to accomplish suitable acceleration and muzzle velocity. A rear face of the cylindrical body may receive substantially all of the propelling force.

In one implementation, according to various aspects of the present invention, an electrode includes a substantially cylindrical body. Prior to launch, the electrode is positioned in a substantially cylindrical tube slightly larger in diameter than the electrode. A propelling force (e.g., rapidly expanding gas) is applied to a rear portion of the tube. The gas pushes against a rear portion of the body of the electrode to propel the electrode out the other end of the tube toward a target.

An electrode includes a shape and a surface area for aerodynamic flight for suitable accuracy of delivery of the electrode across a distance toward a target, for example, about 15 to 35 feet from a launch device to a target. An electrode may rotate in-flight to provide spin stabilized flight. An electrode may maintain its pre-launch orientation toward a target during launch, flight to, and impact with a target.

On impact, an electrode may mechanically couple to a target. Mechanical coupling includes penetrating target tissue or clothing, resisting removal from target tissue or clothing, remaining in contact with a target surface (e.g., tissue, hair, clothing, armor), and/or resisting removal from the target surface. Coupling may be accomplished by piercing, lodging, hooking, grasping, entangling, encircling, adhering, and/or gluing. An electrode, according to various aspects of the present invention, may include structure (e.g., hook, barb, spear, glue ampoule) for mechanically coupling the electrode to a target. A structure for coupling may penetrate a protective barrier (e.g., clothing, hair, armor) on an outer surface of a target. In one implementation, an electrode includes a spear (e.g., pointed shaft, dart point) for penetrating target clothing and/or tissue. A spear extends from the forward portion of the electrode for mechanically coupling to a target. The spear may include a barb for increasing the strength of the mechanical coupling of the electrode to the target.

An electrode is mechanically coupled to a filament to deploy the filament from a wire store and to extend the filament from the launch device to the target. A mechanical coupling may be established between a filament and an electrode in any conventional manner (e.g., threading the filament through a hole in the electrode and knotting the filament to prevent unthreading, tying the filament in a knot to a portion of the electrode, gluing the filament to the electrode, joining (e.g., welding, soldering) a conductive portion of the filament to a metallic portion of the electrode). Mechanical coupling includes coupling a filament and an electrode with sufficient strength to retain the coupling during manufacture, prior to launch, during launch, after launch, during mechanical coupling of the electrode to a target, and while delivering a stimulus signal to a target. According to various aspects of the present invention, suitable mechanical coupling may be accomplished by confining the filament in a portion of the electrode. For example, confining a portion of the filament in an interior of the electrode. Confining may include enclosing, holding, retaining, maintaining mechanical coupling, and/or resisting separation. Confining may be accomplished by preventing or resisting movement or deformation (e.g., stretching, twisting, bending) of the filament. As discussed below, placing the filament in an interior and affixing a spear over the interior in one implementation confines the filament to the interior.

An electrode facilitates electrical coupling of the launch device and the target. Electrical coupling generally includes a region or volume of target tissue associated with the electrode (e.g., a respective region for each electrode when more than one electrode is used). According to various aspects of the present invention, one or more structures of the electrode accomplish lower current density in the region or volume compared to prior art electrodes.

For each electrode, electrical coupling may include placing the electrode in contact with target tissue and/or ionizing air in one or more gaps between the launch device, the deployment unit, the filament, the electrode, and target tissue. For example, a placement of an electrode with respect to a target that results in a gap of air between the electrode and the target does not electrically couple the electrode to the target until ionization of the air in the gap. Ionization may be accomplished by a stimulus signal that includes, at least initially, a relatively high voltage (e.g., about 25,000 volts for one or more gaps having a total distance of about one inch). After initial ionization, the electrode remains electrically coupled to the target while the stimulus signal supplies sufficient current and/or voltage to maintain ionization.

An electrode for use with a deployment unit and/or an electronic weapon, according to various aspects of the present invention, performs the functions discussed herein. For example, any of electrodes 142, 160, 236, 238, 400, and 1018 of FIGS. 1, 2, and 4-10 may be launched from weapon 100 toward a target to establish a circuit with the target to provide a stimulus signal through the target.

Electronic weapon 100 of FIG. 1 includes launch device 110 and deployment unit 130. Launch device 110 includes user controls 112, processing circuit 114, power supply 116, and signal generator 118. In one implementation, launch device 110 is packaged in a housing. The housing may include a mechanical and electrical interface for a deployment unit. Conventional electronic circuits, processor programming, propulsion, and mechanical technologies may be used except as discussed herein.

A user control is operated by a user to initiate an operation of the weapon. User controls 112 may include a trigger operated by a user. When user controls 112 are packaged separately from launch device 110, any conventional wired or wireless communication technology may be used to link user controls 112 with processing circuit 114.

A processing circuit controls many if not all of the functions of an electronic weapon. A processing circuit may initiate a launch of one or more electrodes responsive to a user control. A processing circuit may control an operation of a signal generator to provide a stimulus signal. For example, processing circuit 114 receives a signal from user controls 112 indicating user operation of the weapon to launch an electrode and provide a stimulus signal. Processing circuit 114 provides a launch signal 152 to deployment unit 130 to initiate launch of one or more electrodes. Processing circuit 114 may provide a signal to signal generator 118 to provide the stimulus signal to the launched electrodes. Processing circuit 114 may include a conventional microprocessor and memory that executes instructions (e.g., processor programming) stored in memory.

A power supply provides energy to operate an electronic weapon and to provide a stimulus signal. For example, power supply 116 provides energy (e.g., current, pulses of current) to signal generator 118 to provide a stimulus signal. Power supply 116 may further provide power to operate processing circuit 114 and user controls 112. For hand held electronic weapons, a power supply generally includes a battery.

A signal generator provides a stimulus signal for delivery through a target. A signal generator may transform energy provided by a power supply to provide a stimulus signal having suitable characteristics (e.g., ionizing voltage, charge delivery voltage, charge per pulse of current, current pulse repetition rate) to interfere with target locomotion. A signal generator electrically couples to a filament to provide the stimulus signal through the target as discussed above. For example, signal generator 118 provides a conventional stimulus signal (e.g., 17 pulses per second, each pulse capable of ionizing air, each pulse delivering after ionization about 80 microcoulombs to a human target having an impedance (e.g., after ionization) of about 400 ohms) to electrodes 142 of deployment unit 130 via their respective filaments (e.g., wires in store 140). Signal generator 118 is electrically coupled to filaments stored in wire store 140 via stimulus interface 150.

A deployment unit (e.g., cartridge, magazine) receives a launch signal from a launch device to initiate a launch of one or more electrodes and a stimulus signal to deliver through a target. A spent deployment unit may be replaced with an unused deployment unit after some or all electrodes of the spent deployment unit have been launched. An unused deployment unit may be coupled to the launch device to enable additional electrodes to be launched. A deployment unit may receive signals from a launch device to perform the functions of a deployment unit via an interface.

For example, deployment unit 130 includes two or more cartridges 132-134. Each cartridge 132-134 includes propellant 144, one or more electrodes 142, and wire store 140. A wire store stores a filament for each electrode. Each filament mechanically couples to an electrode as discussed above. Each filament may electrically couple to an electrode as discussed herein. Processing circuit 114 initiates activation of propellant 144 for a selected cartridge via launch signal 152. Propellant 144 propels one or more electrodes 142 toward a target. Each electrode is coupled to a respective filament in wire store 140. As each projectile flies toward the target, each electrode deploys its respective filament out from wire store 140. Signal generator 118 provides the stimulus signal through the target via stimulus interface 150 and the filaments coupled to electrodes 142.

An electrode, according to various aspects of the present invention, may perform one or more of the following functions in any combination: binding the filament to the electrode, deploying the filament, piercing material or tissue at the target, lodging in material or tissue of the target, focusing an electric field prior to ionization or while conducting a stimulus current, forming an ionized path for a stimulus current across one or more gaps, and spreading a current density with respect to a region of target tissue and/or a volume of target tissue.

Figure 1B:
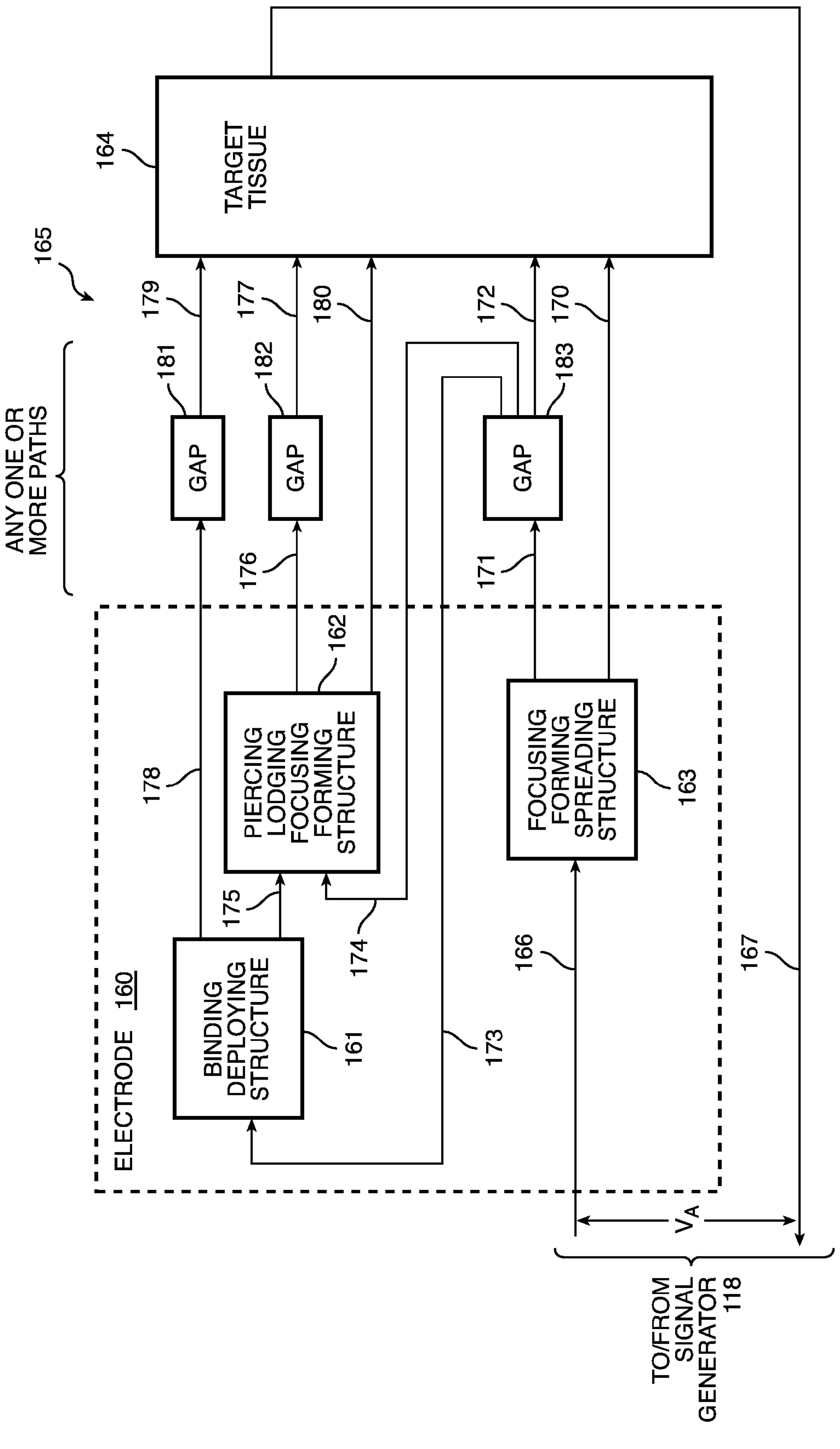
FIG. 1B is a functional block diagram of an electrode of the electronic weapon of FIG. 1A.

For example, electrode 160 of FIG. 1B may be used as an implementation of electrode 142 discussed above. Lines shown on FIG. 1B illustrate paths by which current is conducted through a target 164 (e.g., for ionization, for stimulation also called charge delivery). Arrows on these lines show a single polarity for current flow for clarity of description. Current of any conventional polarity or polarities may flow in one or more directions on any of the lines shown at various times. Electrode 160 includes one or more structures 161 that bind and deploy a filament; one or more structures 162 that mechanically couple the electrode to material (e.g., clothing) or tissue at the target, lodge in such material or tissue, focus an electric field, and form an ionized path for stimulus current; and one or more structures 163 that focus an electric field, form an ionized path for stimulus current, and spread a current density with respect to a region of target tissue and/or a volume of target tissue. Solely for convenience, in the description below, structures 161-163, though plural in some implementations, are referred to in the singular as binding structure 161, mechanical coupling structure 162, and spreading structure 163.

A binding structure has mass, shape, and surfaces for being attached to a filament, for being propelled, and for deploying the filament to a target, as discussed above. Conventional mass, shape, and surfaces may be employed. For example, a binding structure may have a substantially cylindrical mass, an interior with surfaces that grip a filament, and external surfaces with suitable aerodynamic properties for efficient propulsion and accurate flight to a target. A binding structure may include an insulator or consist of insulating material(s). Conventional metal and/or plastic fabrication technologies may be used.

Focusing includes creating electric field flux density. A structure for focusing generally includes a conductive surface having a relatively small radius of curvature since electric field density is increased on curved surfaces (e.g., points, tips, edges, corners). A structure for focusing may be formed of conductive material.

A mechanical coupling structure has a shape suitable for the mechanical coupling method being implemented as well as shape and material suitable for forming ionized paths and conducting stimulus signal current. When adhesion is used for coupling, mechanical coupling structure may have a relatively blunt surface (e.g., relatively large adhering surface) for colliding with material and/or tissue at the target. When piercing and lodging are used for coupling, mechanical coupling structure may have a relatively thin shaft or thin shafts with tips sufficient to pierce material and/or tissue at the target. In the event that a tip of the mechanical coupling structure is the only conductor within range of target tissue (e.g., limited stimulus signal voltage for ionization), such a tip of the mechanical coupling structure has a conducting point to focus electric field flux for ionization of a path to target tissue. At least the point, or most, or all of the mechanical coupling structure may be conductive to receive from the filament the stimulus signal (e.g., current in any polarity) to pass through target tissue. Receiving the stimulus signal is herein called activation of the mechanical coupling structure. A conductive surface of the mechanical coupling structure may be located for focusing to ionize air in a gap to target tissue and/or focusing to ionize air in a gap to another component of an electrode. Such gaps may be omitted when the mechanical coupling structure is positioned against another conductor of the electrode. A mechanical coupling structure may rely on the binding structure to hold the mechanical coupling structure in fixed relation to any of the filament, the spreading structure, and target tissue. A mechanical coupling structure may include an insulator (e.g., a retainer portion gripped by the binding structure, a coating of some or all of the piercing and lodging structures). Conventional metal forming, sharpening, coating, adhesive dispensing, and adhesion technologies may be used.

A spreading structure accomplishes focusing and forming to initiate ionization and accomplishes spreading to deliver the stimulus signal through target tissue. Spreading includes facilitating formation and use of a current path for stimulus signal current in addition to (in parallel with) a current path through a mechanical coupling structure. Spreading includes focusing in a region or volume of target tissue to reduce the electric field flux density that would otherwise occur at the tip of a mechanical coupling structure. A spreading structure may have any shape known in the art for spreading an electric field throughout a region or volume (e.g., antennas, radiators, ionizers, electric field dischargers, igniters, spark shaping apparatus). A spreading structure includes conductive material and may further include insulative material, for example, to inhibit ionization from undesired surfaces and/or locations of the spreading structure. A spreading structure may pierce (e.g., embed, lodge, impale) target tissue. Conventional metal and plastics forming, sharpening, and coating technologies may be used.

A structure involved in forming an ionization path may include materials suitable for experiencing relatively high temperatures. In one implementation, wear of a structure involved in forming one or more ionization paths is facilitated for gathering evidence of use and recording extent of use of an electrode, deployment unit, and/or electronic weapon with a particular target.

In various implementations according to FIG. 1B, structures 161-163 may be implemented with conductive materials and/or nonconductive materials using conventional manufacturing technologies (e.g., casting, machining, crimping, staking, fastening, adhering, assembling) as needed to support conductivity for the desired one or more paths 165. Current paths shown schematically on FIG. 1B adjacent to a gap may be subsumed in structures adjacent to the gap. For example, path 171 in one implementation is implemented as a conductor that extends toward gap 183; yet in another implementation, path 171 corresponds to a conductive portion of spreading structure 163 located adjacent to gap 183. By analogy, paths 173 and 178 may correspond to portions of binding structure 161; paths 174 and 176 may correspond to portions of mechanical coupling structure 162; and paths 172, 177, and 179 may represent portions of target tissue proximate to gaps 183, 182 and 181 respectively. Path 170 may be implemented as a portion of spreading structure 163 that abuts target tissue. Path 175 may represent a joint or abutting contact between binding structure 161 and mechanical coupling structure 162. Path 180 may correspond to a portion of mechanical coupling structure 162 that abuts or impales target tissue 164.

Both mechanical coupling structure 162 and spreading structure 163 may contact target tissue as represented by paths 180 and 170. Paths 180 and 170 may simultaneously conduct stimulus current. Stimulus current consequently divides between paths 180 and 170.

Spreading structure 163 may have the capability to abut target tissue without the capability to pierce and/or lodge in target tissue.

When spreading structure 163 has the capability to pierce target tissue, mechanical coupling structure 162 is preferably designed and/or arranged to be capable of placing a conductive portion of mechanical coupling structure 162 in target tissue to a depth greater than a conductive portion of spreading structure 163.

Either one or both of mechanical coupling structure 162 and spreading structure 163 may be near enough to target tissue that a voltage of the stimulus signal may be sufficient to ionize air in one or both gaps 182 and 183. Paths 177 and 172 may simultaneously conduct stimulus current. Stimulus current consequently divides between paths 177 and 172.

When more than one path of paths 165 is formed, stimulus current divides among the formed paths (an inclusive OR of the paths 165). Due to changes in the environment of the electrode (e.g., movement of the electrode and/or the target with respect to the other), changing signal generator output voltage $V_A$, changes in the conductivity of target tissue), one or more of paths 165 may form, decay, and/or reform over time (e.g., during a series of pulses of stimulus current).

Gap 183 preferably is located between electrode 160 and target 164. In another implementation, gap 183 is located within electrode 160.

An electrode according to various aspects of the present invention may have one or more binding structures 161 (e.g., more than one filament for redundancy, one for each of several stimulus signals), one or more mechanical coupling structures 162 (e.g., increased lodging capability with decreased depth of piercing tissue), and/or one or more spreading structures 163 (e.g., plural spreading structures symmetrically arranged around the shaft of one spear, one or more spreading structures for each of several mechanical coupling structures).

In operation with one of each structure as shown, a voltage $V_A$ is impressed by signal generator 118 across a filament 166 and a return path 167. The return path may be through earth or through a second electrode (not shown) analogous to electrode 160. Current may flow through target 164 by any one or more paths 165. Exemplary paths of paths 165 are described in Table 1. When current flows in more than one path, the current divides among the paths according to numerous factors including the physical dimensions of the electrode, the position and orientation of the electrode with respect to the target, and the nature of the target (e.g., tissue covered with clothing, exposed tissue).

TABLE 1

| Unique Path of Paths 165 | Environment | Path Description |
|---|---|---|
| Gap 181 | Binding structure 161 is proximate to target tissue 164 forming gap 181. Binding structure 161 is proximate to spreading structure 163 forming gap 183. | Voltage $V_A$ is initially sufficient to ionize air in gaps 181 and 183 after which current flows through conductive portions of filament 166, spreading structure 163, gap 183, binding structure 161, gap 181, and target tissue 164 via paths shown schematically as 171, 173, 178, 179, and 167. |
| Gap 182 | Mechanical coupling structure 162 lodges in target clothing forming gap 182 to target tissue. Mechanical coupling structure 162 is proximate to spreading structure 163 forming gap 183. | Voltage $V_A$ is initially sufficient to ionize air in gaps 182 and 183 after which current flows through conductive portions of filament 166, spreading structure 163, gap 183, mechanical coupling structure 162, gap 182, and target tissue 164 via paths shown schematically as 171, 174, 176, 177, and 167. |
| Gap 183 | Mechanical coupling structure 162 lodges in target tissue and spreading structure 163 is located proximate to target tissue forming gap 183. | Voltage $V_A$ is initially sufficient to ionize air in gap 183 after which current flows through conductive portions of filament 166, spreading structure 163, gap 183, mechanical coupling structure 162, and target tissue 164 via paths shown schematically as 171, 172, 174, 180 and 167. |
| Paths 180 and 170 | Mechanical coupling structure 162 lodges in target tissue and spreading structure 163 abuts target tissue. | No ionizing voltage is required. A relatively low stimulus voltage is sufficient to cause stimulus current to flow through conductive portions of filament 166, spreading structure 163, and target tissue 164 via paths 170 and 167. |

Paths 165 represent a set of paths intended to be operable for a particular implementation and set of uses for an electrode according to various aspects of the present invention. As discussed above, a binding structure 161 is conductive. In another implementation, a binding structure 161 is not conductive; consequently, gap 181 and paths 173, 175, 178, and 179 are not used and may be omitted.

In another implementation, a mechanical coupling structure 162 includes nonconductive portions (e.g., insulated conductive material, structure made from insular material) for accomplishing piercing target materials and target tissue and lodging in such materials and/or tissue; and includes conductive portions (e.g., uninsulated conductive material) for accomplishing focusing an electric field and forming an ionized path across a gap.

In yet another implementation, a spreading structure 163 is not intended to operate with a gap 183 to other structures of electrode 160; consequently, gap 183 and paths 171-174 are not used and may be omitted.

In still other implementations, a filament 166 may provide current through a mechanical coupling structure 162 by direct connection or by connection through a resistance (not shown) (e.g., one or more resistors). The resistance may be used to limit division of current through a mechanical coupling structure 162 in favor of unlimited current through a spreading structure 163. The resistance may be implemented as a coating on a conductive portion of a mechanical coupling structure (e.g., coating at least the tip and a forward portion of the shaft of a spear).

Electrode 160, in various implementations according to the present invention, is capable of delivering stimulus current in several different placements of an electrode 160 and a human target 164 wearing clothing. Target tissue includes a relatively lower resistance portion under the skin and a relatively higher resistance associated with abutting the skin or lodging in a superficial portion of the skin. Clothing or other target materials (e.g. matted hair) are assumed to be separated from the skin by a gap of air. Depending, inter alia, on ballistics, placements of mechanical coupling structure 162 (e.g., lodging) may include in target material, in skin of the target, or under the skin of the target. A spreading structure 163 with little or no piercing capability may be in fixed relation to a mechanical coupling structure 162 so as to penetrate target tissue 164 to the same extent as a mechanical coupling structure 162.

Figure 1C:
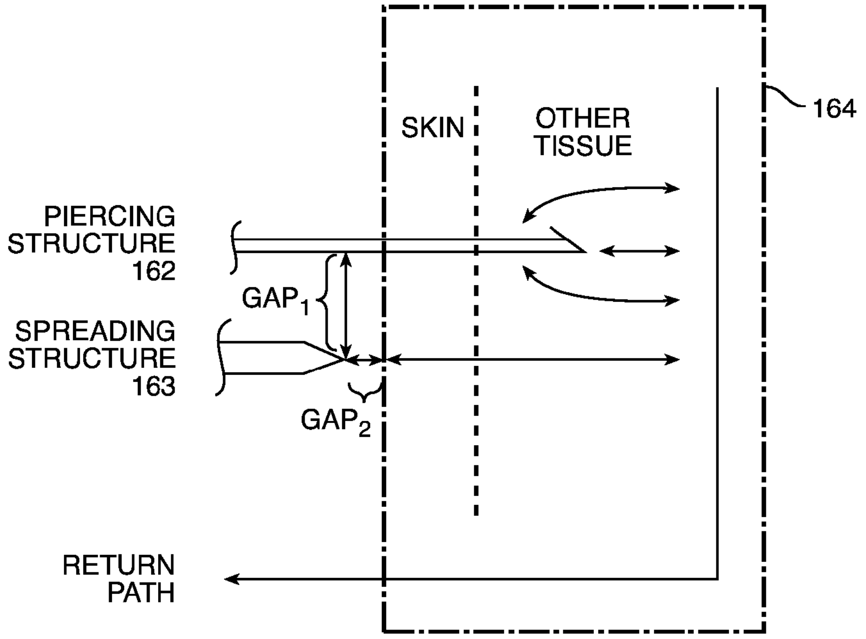
FIG. 1C is a diagram illustrating placement of structures of electrode 160 of FIG. 1B with respect to target tissue.

In another arrangement, e.g., FIG. 1C, a spreading structure 163 is fixed adjacent to a mechanical coupling structure 162. In such an arrangement, after lodging of a mechanical coupling structure 162 in other tissue under the skin of target 164, a spreading structure 163 may attain a placement apart from target skin by a gap ($GAP_2$) containing air and/or target material (as shown), or abutting skin of the target (not shown). Placements of a mechanical coupling structure 162 or a spreading structure 163 are herein defined by the location of a respective conductive portion of the mechanical coupling structure 162 or spreading structure 163 that is closest to the under-skin tissue of the target. Assuming that the portion of a mechanical coupling structure shown in FIG. 1C is conductive material but not connected to filament 166, after ionizing air in a gap ($GAP_1$) from spreading structure 163 to mechanical coupling structure 162 and ionizing air in a gap ($GAP_2$) from spreading structure 163 to target skin, current flows simultaneously as indicated generally by several double arrow lines.

In still another arrangement, a spreading structure makes contact with target tissue. This arrangement is a variation of FIG. 1C in that ionization of $GAP_2$ is not necessary and $GAP_1$ includes target tissue instead of air.

Figure 1D:
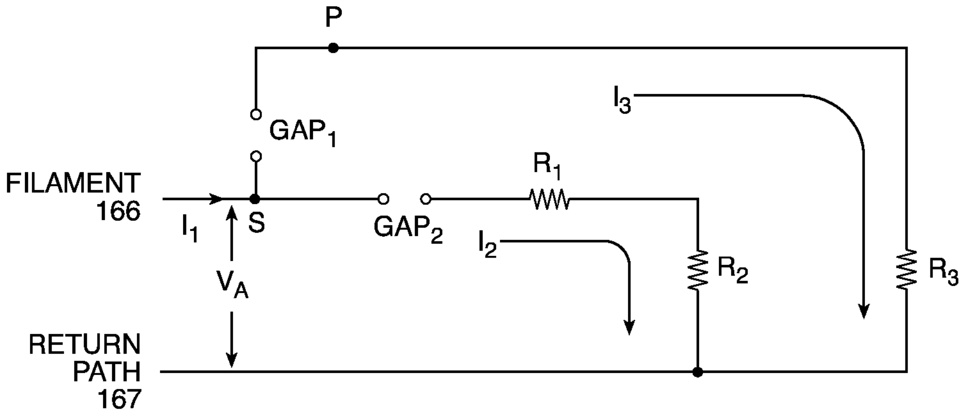
FIG. 1D is a schematic diagram of current paths illustrated in FIG. 1C.

Currents illustrated in FIG. 1C from filament 166 through various structures of electrode 160, through target tissue 164, and the return path 167 flow according to the schematic diagram of FIG. 1D. After voltage $V_A$ ionizes air in gaps $GAP_1$ and $GAP_2$, current $I_1$ divides as $I_2$ through skin resistance $R_1$ and other tissue resistance $R_2$ and as $I_3$ through other tissue resistance $R_3$. Node P is part of mechanical coupling structure 162. Node S is part of spreading structure 163.

Values for the lumped circuit components represented in FIG. 1D may differ over time in one placement of electrode 160. Ionization voltage may be reduced by reducing the dimensions of $GAP_1$ and/or $GAP_2$, and by introducing target tissue instead of air in $GAP_1$.

Figure 2A:
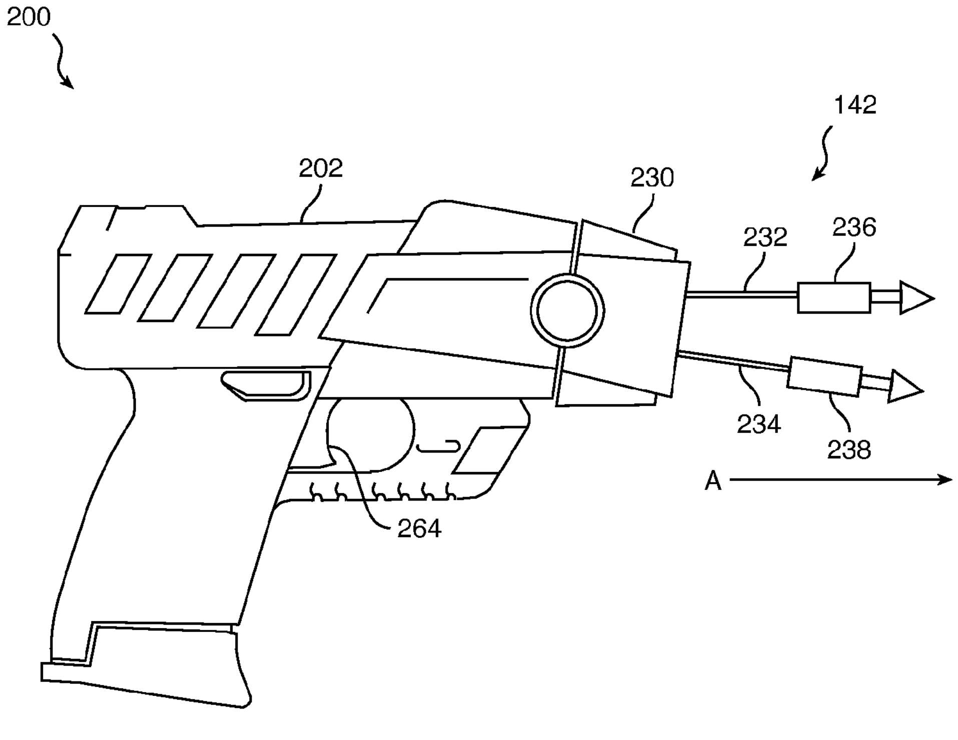
FIG. 2A is side plan view of an implementation of the electronic weapon of FIGS. 1A and 1B.
Figure 2B:
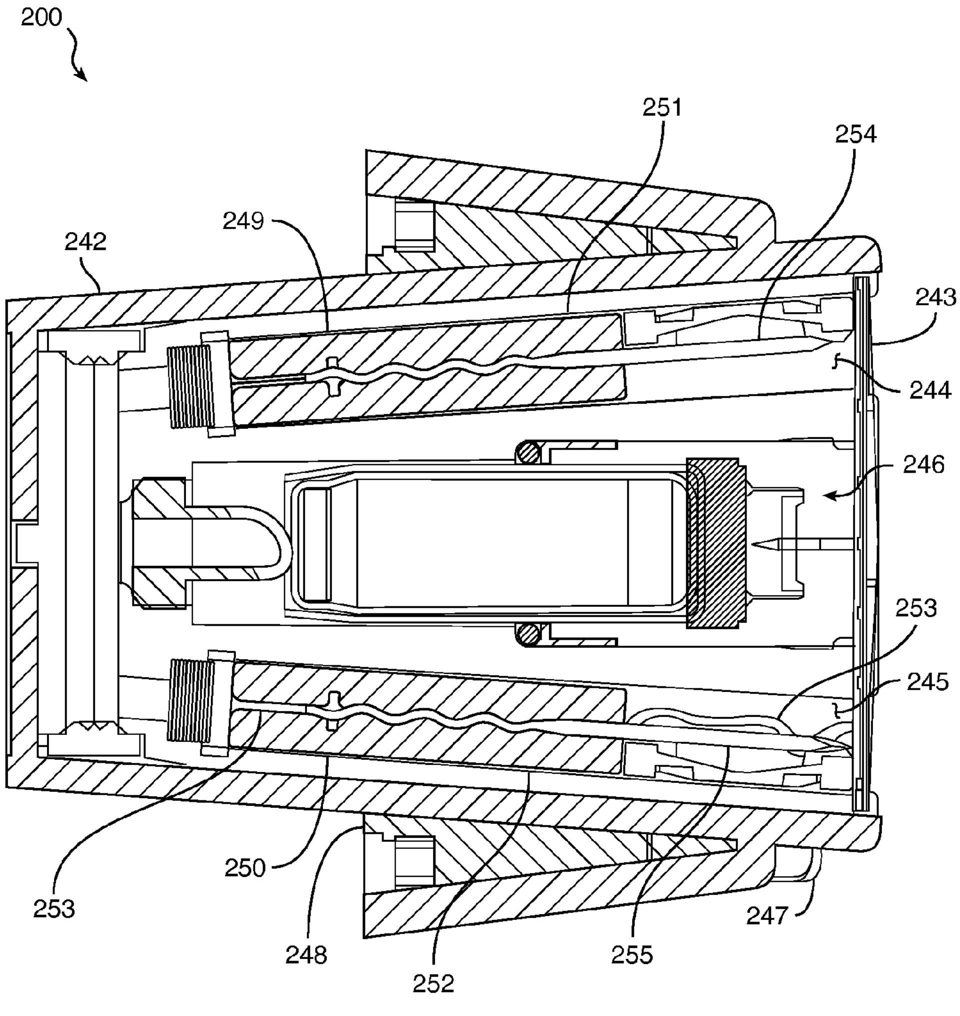
FIG. 2B is a cross-section view of the deployment unit of the electronic weapon of FIG. 2A.

An electronic weapon 100, according to various aspects of the present invention, may launch two electrodes each of the type discussed herein with reference to electrode 160, where one electrode serves in the return path, as discussed above. For example, electronic weapon 200 of FIGS. 2A-2B is shown immediately after a user initiated launch of two electrodes from a deployment unit. Electronic weapon 200 includes a hand-held launch device 202 that receives and operates one field-replaceable cartridge 230 as a type of deployment unit. Launch device 202 houses a power supply (having a replaceable battery), a processing circuit, and a signal generator as discussed above. Launch device 202 may be implemented as a conventional model X26 electronic control device marketed by TASER International, Inc. Cartridge 230 includes two wire-tethered electrodes 236 and 238. Upon operation of trigger 264, electrodes 236 and 238 are propelled from cartridge 230 generally in direction of flight "A" toward a target (not shown). As electrodes 236 and 238 fly toward the target, electrodes 236 and 238 deploy behind them filaments 232 and 234 respectively. When electrodes 236 and 238 are positioned in or near the target, filaments 232 and 234 extend from cartridge 230 to electrodes 236 and 238 respectively. The signal generator provides a stimulus signal through the circuit formed by filament 232, electrode 236, target tissue, electrode 238, and filament 234. Electrodes 236 and 238 mechanically and electrically couple to tissue of the target as discussed above.

A deployment unit may include one or more electrodes as discussed above. For example, deployment unit 230 of FIG. 2B (drawn to scale) includes the exterior dimensions, features, and operational functions, of a conventional cartridge used with model M26 and X26 electronic control devices marketed by TASER International, Inc. For deployment unit 230, each electrode may be propelled from a cylindrical bore in a housing of the deployment unit. For example, deployment unit 230 includes housing 242, cover 243, wire stores (not shown), bores 244 and 245, propellant system 144 comprising separate components, contacts (one shown) 247, and wire-tethered electrodes 238 and 236. Each wire-tethered electrode 238 (236) includes a respective filament (one shown) 234, a respective body 252 (251), and a respective spear 255 (254). Wire stores are located on both sides of the plane of the bores of the housing, so that in the cross section view of FIG. 2B, one wire store is removed by cross section and the other is hidden. Two contacts are located diagonally opposite each other near the corners of rectangular cover 243. The stimulus signal is routed from the launcher through the deployment unit via the contacts. Each contact electrically couples to a respective end of a filament. For example, one end of filament 234 exits a wire store and is held by wedge 248 proximate to contact 247; while the other end of filament 234 passes out of the front of the wire store near cover 243, passes near spear 255, passes along the length of body 252, and enters a rear face of electrode 234 as discussed above. A method of deployment unit assembly includes, inter alia, in any practical order: (a) placing the electrode of the wire-tethered electrode assembly in a bore of the housing, (b) storing the filament in a wire store, and (c) attaching each tether wire to the housing. The method may be practiced, for example, with the structures of FIGS. 2A-2B as suggested in parentheses. The body (252) with spear (255) and filament (234) attached is fed into a bore (245). The filament (234) is neatly placed in a wire store. The loose end of the filament (234) is mechanically coupled near a contact (247) to the deployment unit housing (242) by a wedge (248). The loose end of the filament (234) may abut or be held against the contact (247). A cover (243) is installed to close the bores of the housing 242. A close uniform fit of the body in the bore is desired and accomplished as taught above to facilitate manual and/or automated assembly. Any diameter along the length of the body that exceeds a limit interferes unnecessarily with feeding the body into the bore. In use, the propellant explosively provides a volume of gas that pushes each body 251 (252) from the respective bore 244 (245). Acceleration, muzzle velocity, flight dynamics, and accuracy of hitting the target are affected by the fit of the body as it leaves the bore. Any diameter along the length of the body that exceeds a limit interferes for a period of time unnecessarily with propelling the body from the bore.

Figure 3:
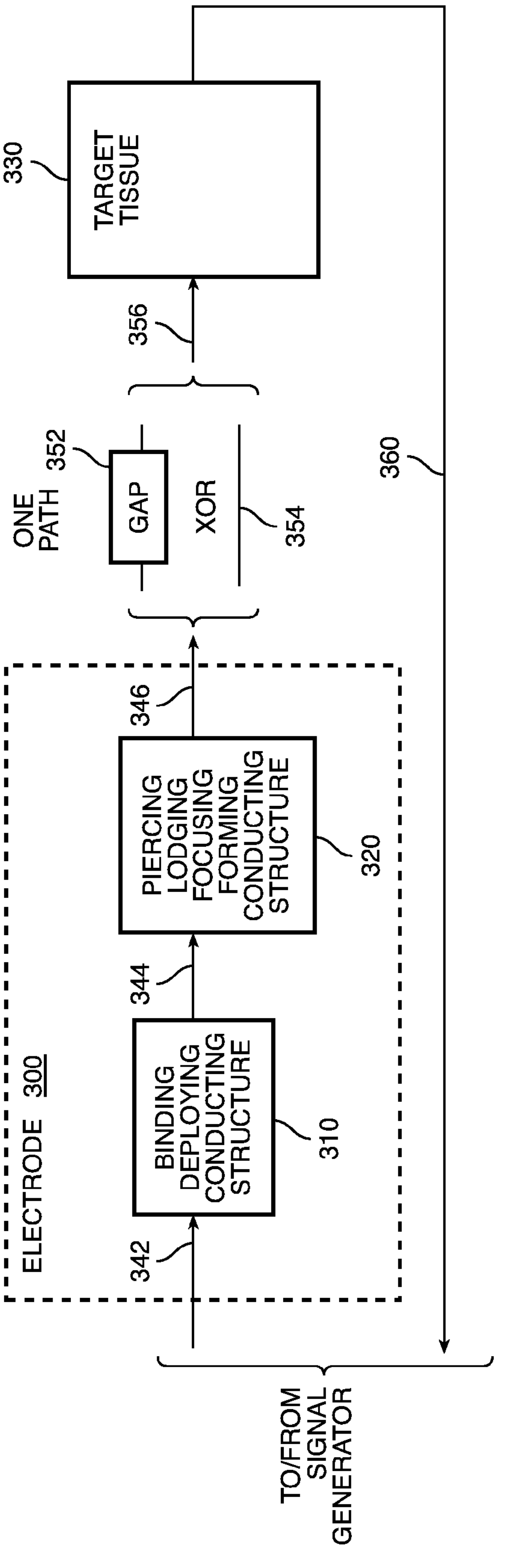
FIG. 3 (RELATED ART)
FIG. 3 is a functional block diagram of an electrode of related art.
Figure 4:
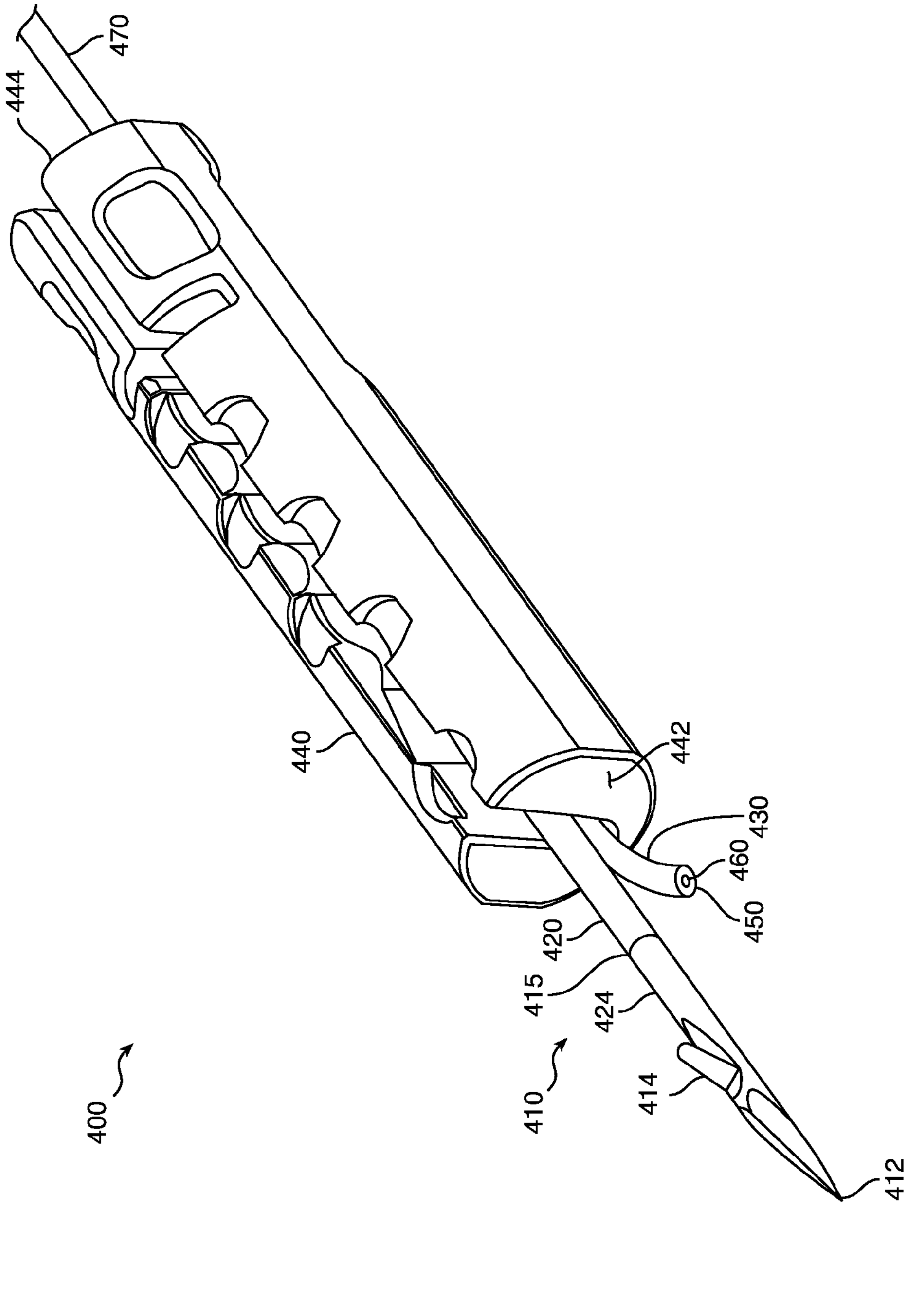
FIG. 4 is a perspective view of an implementation of the electrode of FIG. 1B.
Figure 5:
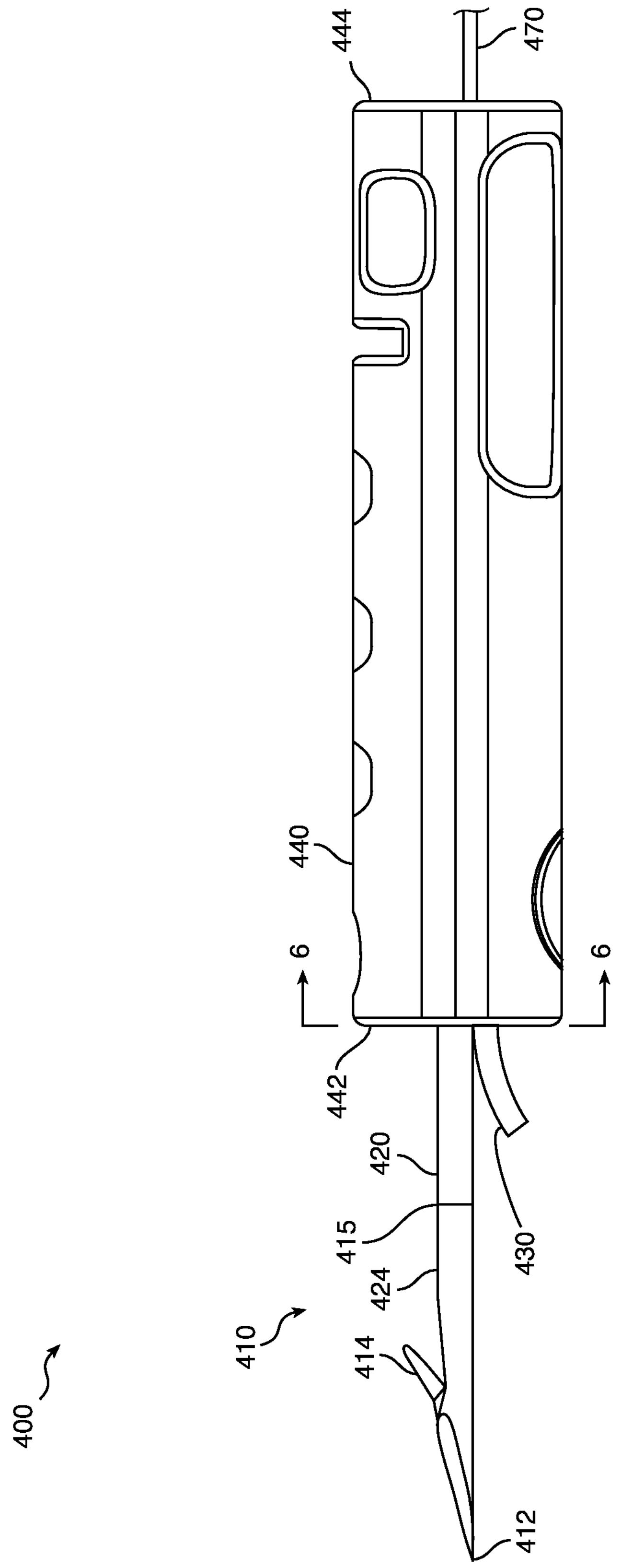
FIG. 5 is a side view of the electrode of FIG. 4.
Figure 6:
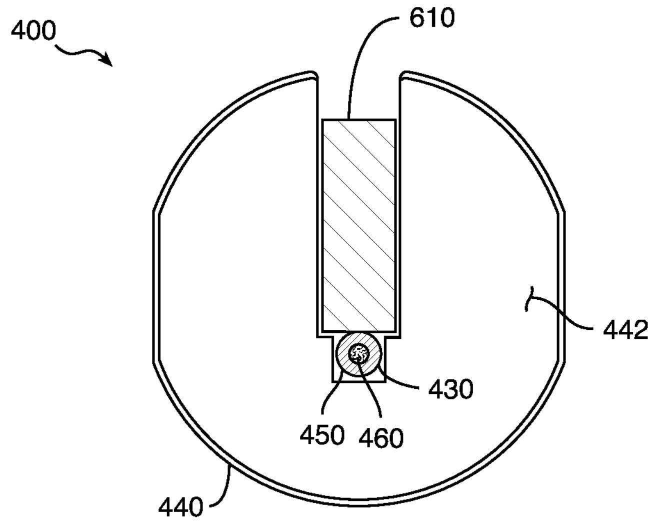
FIG. 6 is a cross-section of the electrode of FIG. 5.
Figure 7:
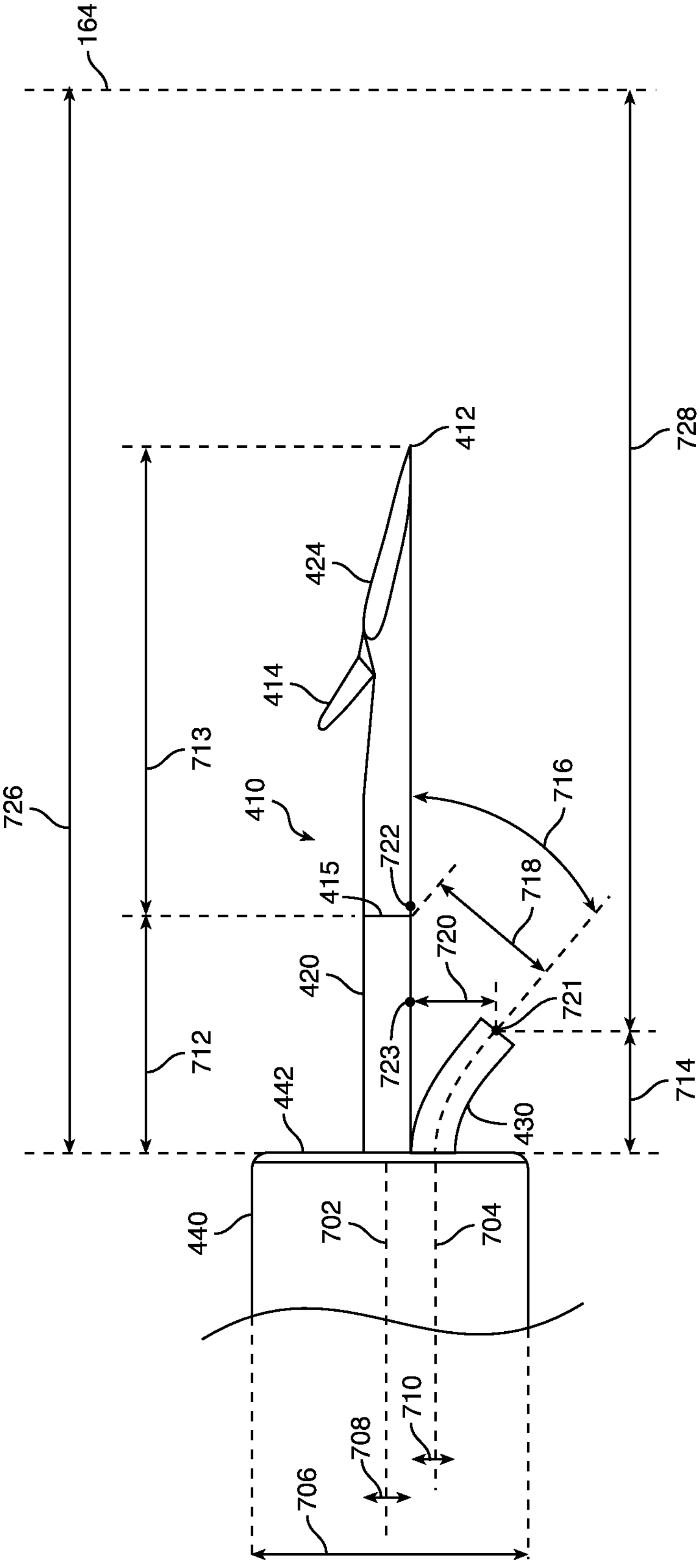
FIG. 7 is a side view of a portion of the electrode of FIG. 4 for defining various dimensional relationships.

In contrast to the electrical coupling discussed above with reference to electrode 160, among other differences, conventional electrodes for electronic weaponry do not perform a spreading function. For example, conventional electrode 300 of FIG. 3 includes a first conducting structure 310 that binds a filament 342 to electrode 300 and deploys the filament 342; and includes a second conducting structure 320 having a tip that pierces target material (not shown) or target tissue 330, lodges in target material (not shown) or target tissue 330, focuses an electric field at the tip, and forms an ionized path across an air gap 352 that may exist between electrode 300 and target tissue 330. Stimulus current is conducted through target tissue 330 on only one of two paths (an exclusive OR of the paths 352, 354). The first alternative path, represented by line 354, occurs when second conducting structure 320 pierces target tissue 330. The second alternative path, represented by gap 352 occurs when second conducting structure 320 does not contact or lodge in target tissue 330 but lodges in material proximate to target tissue close enough to form gap 352.

In one exemplary implementation in accordance with the functions discussed above with reference to FIGS. 1A-1D and 2A-2B, binding structure 161 is implemented as a body, mechanical coupling structure 162 is implemented as a spear, and spreading structure 163 is implemented as a diffuser. The body and spear may be of dissimilar materials. Forming the body comprising a material with significant ductility (e.g., a zinc alloy) may facilitate binding of the filament and/or assembling of the filament and the body. Forming the spear comprising a material with significant hardness (e.g., a stainless steel alloy) may facilitate forming a tip for piercing, lodging, and focusing. At least a portion of the spreading structure facilitates focusing an electric field in or near target tissue. A conductive portion of the spreading structure may be exposed for contact with target tissue. The spreading structure may comprise conductive portions, insulated portions, and portions having one or more pointed surface features. Spreading includes reducing electric field strength (e.g., flux) at the tip of the spear that would occur in the absence of spreading.

In accordance with the functions discussed above with reference to FIGS. 1A-1D, a filament may be bound in the electrode in a manner that accomplishes focusing, forming, and spreading as discussed with reference to spreading structure 163. Prior to assembly with a filament, such an electrode may comprise a binding structure 161 and a mechanical coupling structure 162. After assembly with a filament, such an electrode further comprises a filament that comprises a spreading structure 163. An electrode may be assembled by placing the filament and then the spear through an opening into an interior of the body and shaping the body to interfere with removal of the filament and/or the spear from the interior (e.g., crimping the body, staking the spear into the body, closing the opening of the body, deforming a portion of the body).

Figure 10:
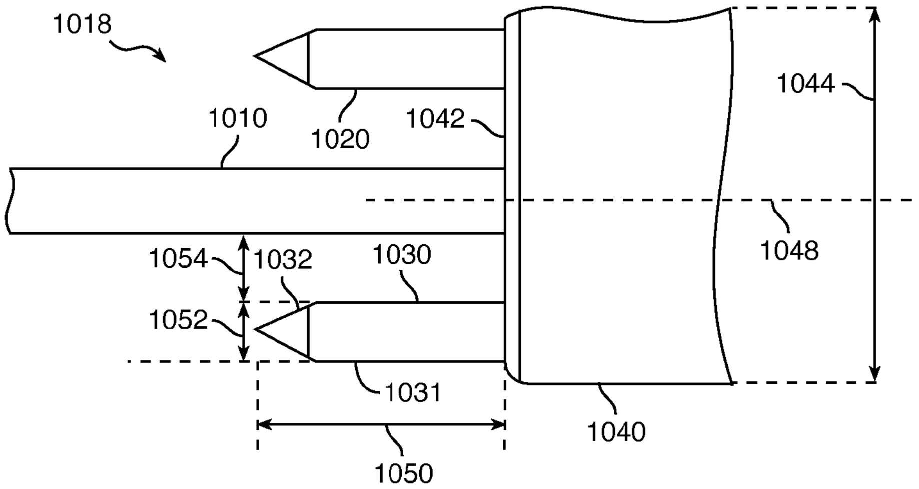
FIG. 10 is a side view of a portion of another implementation of the electrode of FIG. 1B.

A spreading structure distinct from a filament may be used (e.g. FIG. 10). While a portion of the filament may serve as a spreading structure, an additional spreading structure may be used. A filament may be electrically and/or mechanically coupled to a spreading structure.

A body performs the functions of a binding structure as discussed above. A body may have any size and shape known in the art for suitably binding a filament and deploying a filament (e.g., substantially spherical, substantially cylindrical, having an axis of symmetry in the direction of flight, bullet shaped, tear drop shaped). In various implementations, a body may be nonconductive, comprise conductive material, or comprise a combination of one or more conductive portions and one or more insulators.

A spear performs the functions of a mechanical coupling structure as discussed above. A spear may have any size and shape known in the art for suitably piercing material and/or tissue of a target, lodging in material and/or tissue of a target, focusing an electric field for ionization of air in a gap, and forming an ionized path across a gap. In various implementations, a spear may be nonconductive, comprise conductive material, or comprise a combination of one or more conductive portions and one or more insulators. When a spear includes nonconductive (insulative) materials or surfaces, some or all of the focusing and forming functions of electrode 160 may be performed by a spreading structure (diffuser).

A diffuser performs the functions of a spreading structure as discussed above. In one implementation, spreading by a diffuser is uniform across a particular region of target material and/or tissue or is uniform within a particular volume of target material and/or tissue. In another implementation, suitable spreading by a diffuser is not uniformly accomplished. Non-uniform diffusing may result in hot spots of electric field flux with respect to the region of target tissue or volume of target tissue. The hot spots may be distributed, scattered, shaped, bifurcated, and/or segmented. A hot spot is a region or volume in which a local maximum of the electric field flux intensity occurs. A hot spot includes the local maximum and surroundings down to about 80% of the local maximum.

A ratio of the current delivered through target tissue via a mechanical coupling structure to the current delivered through target tissue via a spreading structure is influenced by many factors. For example, factors may include a spatial relationship (e.g., distances between structures, placements) between a spear, a diffuser, and target tissue; a spatial relationship between exposed conductive portions of a spear, a diffuser, a body of the electrode, and target tissue; conductive properties of target tissue, conductive properties of an outer target surface (e.g., clothes, armor); chemical composition of target tissue (e.g., sweat, blood, proximate blood vessel, proximate organ tissue, proximate bone, presence of a drug); movement of the target; and electrical capabilities (e.g., output voltage capability, source impedance, series impedance, output current capability) of the electronic weapon and/or filament.

A spatial relationship between any of a spear, a diffuser, and target tissue may include a physical distance between two of the spear, the diffuser, and target tissue. Such a physical distance may facilitate or limit an electrical relationship between any two of the spear, the diffuser, and target tissue. A description of an electrical relationship includes whether an electrical coupling exists (e.g., via physical contact, via ionization of air in a gap), the magnitude of an impedance of an electrical path, and, if a gap exists, a voltage required to ionize air in the gap.

A change in the spatial relationship between a spear, a diffuser, and/or target tissue may change the electrical relationship between any two of the spear, the diffuser, and target tissue. A change in the electrical relationship may change the ratio of currents provided through the target via the spear and the diffuser.

A spatial relationship may change as an electrode is launched toward a target and mechanically couples to the target. Mechanical coupling includes coupling to an outer target surface, contacting target tissue, and embedding into target tissue. Movement of a target may change the spatial relationship between a spear and target tissue. Target movement may increase a physical distance between a spear and target tissue, move the spear into or out of contact with target tissue, and increase or decrease an amount the spear is embedded into target tissue.

A spatial relationship between a diffuser and target tissue may change as an electrode is launched toward a target and the spear mechanically couples to the target. A diffuser may be positioned a distance away from target tissue with the spear at rest piercing (e.g., embedding) target tissue. A diffuser may contact (e.g., abut) target tissue with a spear at rest piercing target tissue. A diffuser may pierce target tissue with the spear at rest piercing target tissue. The respective conductive portions of a spear and a diffuser may be arranged such that placement of a conductive portion of the diffuser is generally further from non-skin target tissue than placement of a conductive portion of the spear. Resistance $R_3$ of FIG. 1D may be less than resistance $R_2$. Current $I_3$ may be greater than current $I_2$.

A spatial relationship between a diffuser and a spear may change as the diffuser and/or the spear contacts material and/or tissue of a target. A gap of air between a diffuser and a spear (e.g., $GAP_1$) may affect the electrical relationship. A change in the spatial relationship (e.g., length of gap of air) between a diffuser and a spear (e.g., movement of either or both) may affect the electrical relationship.

A diffuser may be flexible (e.g., permanently deformable, resilient). A diffuser may move (e.g., bend, flex, defect, reposition) as the diffuser collides with material and/or tissue of a target. A flexible diffuser may have an initial position with respect to a spear and body of an electrode. The initial position of the diffuser may establish a gap of air of an initial length between the diffuser and the spear. A voltage may ionize the air in the gap of the initial length to establish an electrical coupling between the diffuser and the spear otherwise insulated from each other. Contact of the diffuser with material and/or tissue of the target may move an operative portion of the diffuser away from the spear. As the diffuser moves away from the spear, the length of the gap of air between the diffuser and the spear increases. As the length of the gap of air increases, the electrical relationship between the diffuser and the spear changes.

A diffuser may be inflexible. An inflexible diffuser may be positioned a distance away from a spear to establish a gap of air between the diffuser and the spear. A voltage may ionize the air in the gap to establish an electrical coupling between the diffuser and the spear otherwise insulated from each other. Contact of the diffuser with target tissue may position target tissue in the gap between the diffuser and the spear. Target tissue in the gap may change the electrical relationship between the diffuser and the spear. A diffuser may include a point to aid penetration of target tissue by the diffuser, to focus an electric field, to form an ionized path, and/or to spread an electric field. A diffuser may include a barb to lodge in (e.g., resist removal from) material and/or tissue of the target. A diffuser may include one or more conductive and insulative portions for shaping an electrical field of the diffuser.

An electrode may include one or more insulators. An insulator includes any material (e.g., insulative, insular, insulation) that significantly interferes with operative conduction. Air may serve as an insulator over a distance having a breakdown voltage greater than voltages of the stimulus signal. An insulator may be implemented as a structure of the electrode (e.g., shaft of a spear, shaft of a diffuser) and/or as a coating of a structure of the electrode. The coating may be uniform. The coating may be partial or non-uniform. Insulative coatings include lacquer, black zinc, a dielectric film, a non-conductive passivation layer, a polyp-xylylene polymer (e.g., Parylene), polytetrafluoroethylene (e.g., Teflon), a thermoplastic polyamide (e.g., Zytel). Insulative structures may comprise plastic, nylon, fiberglass, or ceramic. Conventional insulative technologies may be used.

An electrode may include one or more diffusers. Diffusers of the same electrode may differ (e.g., length, flexibility, position relative to a spear, position relative to insulators, position relative to a body of the electrode, impedance, material composition). Each diffuser may provide a portion of a current through a target. Diffusers may differ in respective spatial relationships between the diffuser, other portions of the electrode, and/or target tissue.

A diffuser may be formed of conventional material(s) suitable for spreading current into, in, and/or through target materials or tissue (e.g., conductive and/or insulative). A diffuser, as discussed above, may provide the current to target tissue by abutting target tissue, provide current to target tissue via ionized air in a gap between the diffuser and target tissue, and/or provide current to target tissue via ionized air in a gap between the diffuser and a spear positioned in or near target tissue.

An insulated conductor incorporated into a structure of an electrode may provide a current through a target via an exposed portion of the conductor (e.g., not covered, non-insulated, insulator designed to be defeated under desired conditions). An exposed portion of the conductor may provide a current directly to target tissue or provide a voltage suitable for ionizing air in a gap between the exposed portion of the conductor, target tissue, and/or another conductive structure of the electrode.

In one implementation, the diffuser is implemented as part of a filament. An axial filament (e.g., tether wire), axially insulated, has a trans-axial cut end that exposes the conductor of the filament. The cut end and a portion of the filament back from the cut perform the functions of a diffuser as discussed above. For example, cutting a filament to length generally exposes the conductor at the cut end of the filament. The cut end and a portion of the filament, may be positioned so that the cut end lies a distance away from a conductive portion of the spear. A voltage of the stimulus signal may ionize air in the gap between the conductor of the filament and the conductive portion of the spear to establish an electrical coupling for a duration of ionization in the gap. Due to the small dimensions of the gap between the conductor of the filament and the spear, a relatively low voltage (e.g., 200V-400V) stimulus signal may ionize air in the gap.

Ionizing air in a gap to establish a path between a diffuser and at least one of another structure of the electrode and target tissue may increase a temperature of the diffuser. An increase in temperature may melt a portion of the diffuser (and other structure of the electrode). Melting an insulator may deform the shape of the insulator. Melting a conductor, in particular through a rapid increase in temperature, may vaporize, pit, and/or score a portion of the conductor and/or deposit a carbon build-up on a portion of the conductor.

Each time air in a gap is ionized to provide a pulse of current, according to various aspects of the present invention, a predictable portion of a conductor and/or an insulator is melted resulting in a cumulative and measurable indication (e.g., record, sign, evidence) of providing the pulse of current (e.g., a portion of a stimulus signal). Analysis of such indicia may provide information about a use of an electronic weapon. For example, a method according to various aspects of the present invention for determining the extent of current provided by an electrode as discussed herein includes comparing a subject structure of the electrode from which an ionized path was formed during provision of the current with a set of reference structures of the same construction. The members of the set have classified amounts of wear. A result of comparing facilitates determining the classification of the subject structure (e.g., more wear than one member of the set and less wear than another member of the set) and consequently determining the likely extent of current provided by the subject electrode.

An electrode, according to various aspects of the present invention, may include a body, one or more spears, and one or more diffusers. A body may include an insulated portion (e.g., one or more insulators). A spear may include an insulated portion (e.g., one or more insulators). A diffuser may include an insulated portion (e.g., one or more insulators). A filament may be insulated from other structures of the electrode. Insulated portions generally limit current path formation and/or focus electric fields for path formation and current spreading.

A body includes a forward portion (e.g., front face) with respect to a direction of flight (e.g., FIG. 2A direction A) toward a target and a rear portion (e.g., rear face). A body mechanically couples to a spear and to a diffuser. The forward portion of the body is generally oriented toward a target prior to launching the electrode, during flight of the electrode toward the target, and after the electrode mechanically couples to the target. With reference to the direction of flight toward a target, a body is positioned behind a tip of the spear and behind the exposed conductor of the diffuser. A body mechanically couples to a filament. A body may include a substantial portion of the total mass of the electrode. A body provides a surface area for receiving a propelling force to propel the electrode toward a target. A body is propelled away from a deployment unit responsive to a propelling force. In an implementation where the body comprises a conductive portion or is entirely conductive, the body positioned proximate to target tissue may electrically couple to a target.

A spear mechanically couples to a body of an electrode. A spear may extend from a forward portion of the body. A spear may mechanically couple an electrode to a target. A spear may penetrate a protective barrier on an outer surface of a target. A spear may penetrate target tissue. A spear may resist decoupling from a target. A spear may deliver a stimulus signal through a target. A spear may electrically couple to a diffuser as discussed herein. A spear may electrically couple to the body. A spear may mechanically couple to the diffuser.

A diffuser may mechanically couple to a body of the electrode. A diffuser may extend away from a forward portion of the body toward the target. A diffuser may conduct a portion of the current through the target. A diffuser may electrically couple to a spear and/or a target as discussed above. A diffuser may electrically couple to the body of the electrode. A diffuser may mechanically couple to a spear. A diffuser may mechanically couple to target tissue. A diffuser may electrically couple to a filament.

A diffuser may be flexible or inflexible. A diffuser may be positioned with respect to the body, the spear, and/or the target. Placement of an electrode in or near a target may change the position of the diffuser with respect to the body, the spear, and/or the target. An electrical coupling between the diffuser, the body, the spear, and/or the target may depend, at least in part, on a position of the diffuser with respect to the body, the spear, and/or the target.

An insulator may reduce a likelihood of establishing an electrical coupling. An insulator may influence formation of an ionization path through air in a gap between the spear and the diffuser. An insulator may establish a physical relationship between a diffuser, a spear, a body, and/or a target to provide a current through a target via the spear, the diffuser, and/or the body. An insulator may establish a gap of air between a spear and a diffuser.

A spear may include an insulator. An insulator may insulate all or any portion of a spear. A spear may be partially or entirely formed of a material that electrically insulates. An insulator may be of a type (e.g., thickness, material, structure) that electrical insulates the spear against a current having a voltage below a threshold, but fails to insulate the spear against a current having a voltage above the threshold. An insulator may be formed (e.g., shaped, applied, positioned, removed, partially removed, cut) to establish a likely location on the spear where the insulator may fail to insulate against a current having a voltage above a threshold. An insulator may be positioned on or near a spear relative to a diffuser.

A diffuser may include an insulator. An insulator may insulate all or any portion of a diffuser. A diffuser may be partially formed of a material that electrically insulates. An insulator may be of a type (e.g., thickness, material, structure) that electrical insulates the diffuser against a current having a voltage below a threshold, but fails to insulate the diffuser against a current having a voltage above the threshold. An insulator may be formed to establish a likely location on the diffuser where the insulator may fail to insulate against a current having a voltage above a threshold. An insulator may be positioned on or near a diffuser relative to a spear.

A tip (e.g., point, cone, apex comprising acute angles between faces, end of a shaft of relatively small diameter) operates to pierce an outer surface (e.g., layer) of a target and/or target tissue. A tip of a spear facilitates piercing, lodging, focusing, and forming by a spear. A tip of a diffuser facilitates focusing and forming by a diffuser. A tip when insulated may operate as a gap or switch interfering with current flow (e.g., blocking) until a threshold voltage breaks down the insulator and permits ionization near the tip and/or current flow through the tip.

A barb operates to lodge (e.g., retain) an electrode in material and/or tissue of a target to retain a mechanical coupling between the barb and the material and/or tissue. A barb portion of a spear resists mechanical decoupling (e.g. removal from material or tissue). A barb portion of a diffuser resists mechanical decoupling of a diffuser from material and/or tissue of a target.

A stimulus signal through a target may be diffused by an electrode, according to various aspects of the present invention, so that current of the stimulus signal flows in multiple paths through target tissue, or flows through multiple portions of target tissue in a single path.

A path may include an electrical coupling established through physical contact of two conductors and/or ionization of air in a gap between two conductors. A gap may include target tissue.

Electrode 400 of FIGS. 4-11 performs the functions of an electrode discussed above with reference to FIGS. 1A-1D. Electrode 400 after assembly with filament 470 includes body 440, spear 410, and diffuser 430.

Filament 470 extends from rear portion 444 of body 440 to couple electrode 400 to signal generator 118 of electronic weapon 100. Signal generator 118 provides a stimulus signal through filament 470 to electrode 400. Filament 470 is an insulated conductor and mechanically couples to body 440 as discussed above when electrode 400 is assembled. In the absence of a stimulus signal, filament 470 is not electrically coupled to body 440 or spear 410. In one implementation, the diameter of filament 470 is about 0.015 inch with an internal copper clad steel conductor of about 0.005 inch. In another implementation, the diameter of filament 470 is about 0.018 inch.

Body 440 includes forward portion 442 and rear portion 444, both with reference to the direction of flight of electrode 400 toward a target. Body 440 mechanically couples to spear 410. Body 440 may electrically couple to spear 410. Body 440 may include an interior into which a filament and a spear are introduced. The interior may be closed in any conventional manner. In one implementation, body 440 is a soft metal alloy (e.g., a zinc alloy) facilitating deformation to close the interior. In one implementation, body 440 has a diameter of about 0.213 inch.

Spear 410 is formed of any conventional electrically conductive material (e.g., metal, semiconductor, superconductor, nano-material), for example, stainless steel. Spear 410 includes tip 412 and barb 414. Spear 410 may include an insulator on or comprising one or more portions (420, 424, and/or 412) of spear 410. In another implementation, insulators are omitted and spear 410 has a conductive surface (e.g., 412, 424, 420). Tang 610 (FIG. 6) of spear 410 mechanically couples spear 410 to body 440. Spear 410 may electrically couple to body 440. Spear 410 extends forward with respect to the direction of flight toward a target from forward portion 442 of body 440 toward a target. In one implementation, spear 410 has a diameter of about 0.035 inch and a length of from about 0.25 to about 0.55 inch, preferably about 0.40 inch.

According to various aspects of the present invention, diffuser 430 comprises an end portion of filament 470. Filament 470 enters rear portion 444 of body 440, passes through the interior of body 440 and extends out from forward portion 442 of body 440. End portion of filament 470 extends forward of forward portion 442 and performs the functions of a diffuser as discussed herein.

Various dimensions of electrode 400 and its components affect operation of diffuser 430. Body 440 has diameter 706 (FIG. 7) about a central axis of symmetry 702. Spear 410 has a diameter 708 about a central axis of symmetry that coincides with axis 702. Filament 470 has a diameter 710 about a central axis of symmetry 704. Axis 704 follows the center of the conductor of diffuser 430 through operating point 721 for defining various distances and angles effecting diffuser functions including focusing, forming, and spreading, as discussed above.

Diffuser 430 includes insulator 450 and conductor 460. Insulator 450 encases conductor 460. Insulator 450 insulates conductor 460 from electrically coupling to body 440 and spear 410 via physical contact between conductor 460 and body 440 or spear 410. Diffuser 430 comprises an operating point 721 comprising the uninsulated end of conductor 460, cut to expose conductor 460 to the atmosphere. The end portion of filament 470 is formed on a curve about a radius described generally as an angle 716 of a tangent to the curve with respect to spear 410 (e.g., in a direction of flight). Angle 716 is sufficient to cause operating point 721 to move away from spear 410 on impact with target material and/or tissue, for example, in the range of 10 degrees to 90 degrees, preferably about 45 degrees.

Diffuser 430 and its operating point 721 are formed and given an initial position so that in use, operating point 721 creates one or more ionized paths for stimulus signal current. Preferred positioning may make paths through target tissue more likely than paths through spear 410; and/or may make paths through spear 410 more likely than paths through body 440 when body and spear are electrically coupled. For ease of manufacturing, filament 470 may be cut at a tangent to body 440 to form diffuser 430. Generally, increasing the forward reach 714 of diffuser 430 with respect to body 440 reduces the likelihood of ionization from diffuser 430 to body 440 (also called back activation). Generally, increasing the standoff distance 720 of diffuser 430 from spear 410 reduces the likelihood of ionization from diffuser 430 to spear 410 and increases the likelihood of an ionization path through target tissue. For a spear comprising an insulative rearward portion having a length 712 and a conductive forward portion having a length 713, generally increasing the length 712 increases the likelihood of ionization from diffuser 430 to target tissue.

For example, diffuser 430 may be cut to a length so that while diffuser 430 is pressed against (e.g., parallel to) front portion 442 (e.g., angle 716 is about 90 degrees), diffuser 430 does not extend beyond or wrap around body 440. When body diameter, distance 706, is about 0.213 inch, spear diameter is about 0.035 inch, and filament 470 is juxtaposed against spear 410, diffuser 430 is cut at a tangent to body 440, for a length (e.g., when straightened) of about 0.089 inch from front portion 442 of body 440. Consequently, depending on angle 716, the forward reach, distance 714, to operating point 721 is in the range of half the diameter of filament 470 (e.g., 0.0075 inches) to half the diameter of body 440 (e.g., 0.107 inches), preferably about 0.089 inches. When angle 716 is about 45 degrees, forward reach 714 is about 0.063 inches. Increasing the length of diffuser 430 may reduce the likelihood of ionization between operating point 721 and body 440, for instance, when angle 716 is about 90 degrees.

The conductive portion of the spear that is closest to the operating point of the diffuser is herein called the location of spear activation. When the shaft portion of a spear comprises uninsulated conductive material, the location of spear activation, for example, may be a distance 720 from operating point 721 to the nearest point 723 on spear 410. A spear may comprise a rearward portion and a forward portion. For example, spear 410 includes rearward portion 420 having length 712 from the forward portion 442 of body 440 to a boundary 415 and further includes a forward portion 424 having length 713 from boundary 415 to tip 412. In an implementation where rearward portion 420 has a nonconductive exterior surface (e.g., comprises an insulator, a conductor covered with an insulator), and forward portion 424 has a conductive exterior surface, the location of spear activation, may be a distance 718 from operating point 721.

In an implementation having a conductive body 420 electrically coupled to spear 410, a forward activation distance 718 may be less than a backward activation distance 714 to increase a likelihood that spear activation occurs through or near target tissue.

A distance from a location of spear activation 723 to the operating point 721 of diffuser 430 defines a standoff distance 720. According to various aspects of the present invention, a standoff distance is greater than half the diameter of filament 470 (e.g., small angles 716) and less than the length of diffuser 430 (e.g., large angles 716). In one implementation distance 720 is about 0.05 inches when angle 716 is about 45 degrees, diameter of filament 470 is about 0.015 inches, diffuser length is about 0.089 inches, and forward activation distance 718 is about 0.089 inches.

A diffuser may be designed to deform on impact with a target (e.g., ductile, flexible). The position of the operating point of a diffuser relative to other portions of the electrode (e.g., a standoff distance) may change on impact and/or penetration of the target from an initial position set by manufacturing of the electrode and prior to deployment. For example, penetration of spear 410 into target 164 (tissue or material) may change a position of diffuser 430 with respect to spear 410 and body 440. Such a change in position may include a change in angle 716, a change in standoff distance 720, a change in forward activation distance 718, and/or a change in backward activation distance 714. A change in position generally changes one or more electrical relationships between operating point 721, spear 410, body 440, and target tissue 164. These electrical relationships may determine which one or more of several possible ionization paths becomes ionized and conducts current of the stimulus signal. Generally a shorter path is ionized and a longer path is not ionized.

Examples of dimensions, electrode placements, and operation of an electrode 400 are described in Table 2. In this implementation, body 440 is electrically coupled to spear 410 in the interior of body 440. Spear 410 has a conductive surface (e.g., spear is stainless steel) from forward portion 442 to tip 412. Nevertheless, tip 412 has a voltage with respect to the return path only after (a) conduction from operating point 721 through target tissue; (b) ionization from operating point 721 to target tissue, to spear 410 (e.g., forward activation), and/or (c) ionization to body 440 (e.g., backward activation).

TABLE 2

| Row | Dimensions | Placement | Operation with Respect To Return Path |
|---|---|---|---|
| 1 | before impact, standoff distance 720 is approximately the same as forward reach distance 714; after impact, distance 728 < standoff distance 720 and distance 728 < distance 714 | spear 410 lodges in target tissue | forward activation with spreading; stimulus current spreads at least between a first path from operating point 721 through target tissue and a second path from operating point 721 to spear activation point 723 then through tip 412 and tissue; second path may also include target tissue between point 721 and point 723. |

TABLE 2-continued

| Row | Dimensions | Placement | Operation with Respect To Return Path |
|---|---|---|---|
| 2 | before impact, standoff distance 720 is approximately the same as forward reach distance 714; after impact distance 714 < distance 720; distance 728 similar to distance 714 | spear 410 pierces target material, deforms diffuser 430, and pierces target tissue | backward activation with spreading; stimulus current spreads at least between a first path from operating point 721 to body 440 then through tip 412 and tissue and a second path from operating point 721 through target tissue |

During impact with a target, electrode 400 may perform spreading initially according to row 1 of Table 1 and subsequently according to row 2 of Table 1 due to inertia of impact and/or motion of the target.

In another implementation, spear 410 includes insulated rearward portion 420, boundary 415, and uninsulated forward portion 424 as discussed above. Body 440 is not electrically coupled to spear 410 in the interior of body 440. Insulator 420 may be formed of any conventional electrically insulating material including those discussed above. For example, the diameter of the insulated portion 420 of spear 410 may be about 0.035 inches. Examples of dimensions, electrode placements, and operation of this implementation of an electrode 400 are described in Table 3.

TABLE 3

| Row | Dimensions | Placement | Operation with Respect To Return Path |
|---|---|---|---|
| 1 | before impact standoff distance 720 is approximately the same as forward reach distance 714; after impact, distance 728 < standoff distance 720 and distance 728 < distance 714; distance 726 is less than distance 712; distance 718 is greater than distance 720 | rearward portion 420 is in target tissue | forward activation with spreading; stimulus current spreads at least between a first path from operating point 721 through target tissue and a second path from operating point 721 to spear activation point 722 then through tip 412 and tissue; second path includes target tissue between point 721 and point 722. |

An insulator may be applied to a surface of spear 410 to form insulator 420. For parylene insulation, a thickness of an applied insulator is in the range of 0.1 micrometers to 76 micrometers, preferably 60 micrometers thick.

A shape of spear 410 may affect the performance of insulator 420. For example, the size and geometry of tip 412 or barb 414 of spear 410 may limit a thickness of an applied insulator. A reduction in the thickness of insulator 420 at a position on spear 410 may reduce the capacity of the insulator proximate to tip 412 and/or barb 414 to resist a current flow through spear 410. Application of a voltage to spear 410 greater than a threshold may break down insulator 420 near tip 412 or barb 414 to permit a current to flow through spear 410 into a target.

A diffuser, according to various aspects of the present invention, may provide evidence of providing a current through a target as discussed above. When substantially all current through a diffuser is conducted via ionization of a gap at a conductor of a diffuser, the extent of pitting of the conductor may be directly proportional to current delivered through target tissue. When substantially all current through a diffuser is conducted via ionization of a gap at an insulator of a diffuser, melting of the insulator may be directly proportional to current delivered through target tissue.

Figure 8:
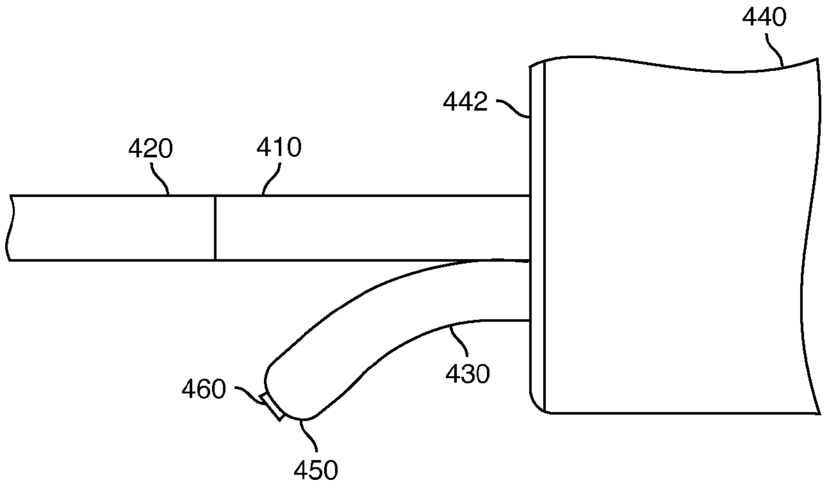
FIG. 8 is a side view of a portion of the electrode of FIG. 5 after providing current.
Figure 9:
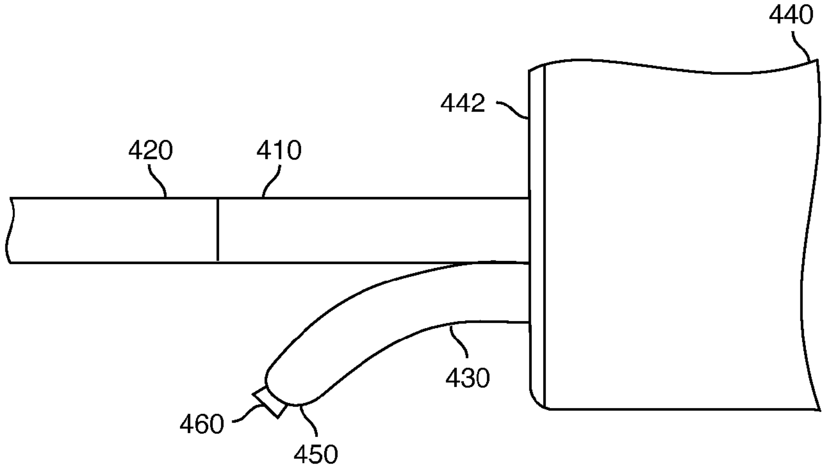
FIG. 9 is a side view of a portion of the electrode of FIG. 8 after providing additional current.

For example, prior to providing a current through a target, insulator 450 and conductor 460 of diffuser 430 have the appearance of a newly manufactured filament. A newly manufactured diffuser lacks pitting, scoring, melting, and other physical evidence of providing a current on the insulator and on the conductor of the diffuser. For example, a tip of diffuser 430 is formed by cutting filament 470 orthogonally to the length of filament 470. Prior to carrying a current, conductor 460 is visible only by viewing the tip of diffuser 430 looking into the length of diffuser 430 and the edge of insulator 450 forms about a 90-degree angle. As diffuser 430 provides a current, conductor 460 and insulator 450 may be heated by ionization and arcing of the current across a gap of air. As such a current continues to be delivered via diffuser 430, insulator 450 melts, rounding cut edges of conductor 450 and exposing conductor 460 as shown in FIG. 8. Continued delivery of such a current through diffuser 430 results in additional melting and rounding of insulator 450 and additional exposure of conductor 460 as shown in FIG. 9. The amount of rounding of insulator 450 and exposure of conductor 460 is proportional to the amount of current delivered via diffuser 430. When the current is delivered in pulses of substantially equal charge, the amount of rounding and exposure may correlate to the quantity of pulses of current delivered through target tissue.

Delivery of a current through diffuser 430 may alter a surface of insulator 450 and conductor 460. Delivery of a current through diffuser 430 results in pitting, scoring, vaporization, and carbon build-up on the surface of insulator 450 and conductor 460. The amount of alteration of the surface of insulator 450 and conductor 460 is proportional to the amount of current delivered and/or a quantity of pulses of current delivered through diffuser 430 as discussed in the articles incorporated by reference above.

Analysis of insulator 450 and conductor 460 provides evidence of a quantity of current that was delivered through a target.

The amount of pitting, scoring, vaporization, and carbon build-up on the surface of insulator 450 and conductor 460 is proportional to a quantity of times ionization occurred during delivery of a stimulus signal. Forming a diffuser to a shape prior to use provides a benchmark in measuring and comparing a delivery of current through an electrode. Preferably, a tip of a diffuser is formed to have regular (e.g., orthogonal) edges as discussed above.

In another implementation of an electrode, according to various aspects of the present invention, the electrode includes a diffuser that is not intended to be deformed on impact with a target. Because the position of the operating point of such a diffuser is maintained with respect to other components of the electrode, an electrode may comprise more than one such diffuser. For example, electrode 1018 of FIG. 10 includes body 1040, spear 1010, a first diffuser 1020, and a second diffuser 1030. Electrode 1018 performs the functions of an electrode 160 as discussed above. Body 1040, spear 1010, and diffusers 1020 and 1030 respectively perform the functions of a body, a spear, and a diffuser respectively as discussed above. For instance, body 1040 may be implemented in a manner similar to body 440 except that a filament (not shown) is electrically coupled to diffusers 1020 and 1030, insulated from body 1040, and insulated from spear 1010 in the absence of ionization.

Body 1040 may be formed to facilitate ionization between a filament and a diffuser in the interior of body 1040. Located at least a part of the ionization in a controlled environment facilitates correlation of changes to a conductor (e.g., filament, diffuser, additional surface within body 1010) and/or to an insulator (filament, diffuser, additional insulator within body 1010) with an amount of current delivered through a diffuser.

Spear 1010 may be formed of electrically conductive material (e.g., stainless steel), formed of insulating material, or formed of a combination of conducting and insulating materials as discussed above. For clarity of description, spear 1010 comprises conductive material proximate to diffusers 1020 and 1030 in the discussion below.

Spear 1010 includes a tip and a barb (not shown) analogous to spear 410. Spear 1010 is mechanically coupled to body 1640 in any conventional manner. Spear 1010 may electrically couple to body 1040. Spear 1010 extends forward from forward portion 1042 of body 1040 with respect to the direction of flight toward a target.

In one implementation, spear 1010 is entirely insulated to facilitate spreading of current from diffusers 1020 and 1030 through target tissue. In such an implementation, spear 1010 does not perform focusing, forming, or conducting functions.

A diffuser may perform a binding function in addition to or in place of a binding function of a body. When a diffuser is mechanically fixed to a body, mechanical coupling of a filament to a diffuser binds the filament to the body.

Diffusers 1020 and 1030 are arranged symmetrically with respect to at least one of forward portion 1042 of body 1040, spear 1010, and an axis of central symmetry 1048 of body 1040 and/or spear 1010. Diffusers 1020 and 1030 may be structurally and functionally identical as shown. By symmetric arrangement, proximity of at least one diffuser and material or tissue of the target is facilitated.

Diffuser 1030 is formed of any conventional electrically conductive material. Diffuser 1030 mechanically couples to forward portion 1042 of body 1040. Diffuser 1030 extends forward of forward portion 1042. Diffuser 1030 does not electrically couple to body 1040 or spear 1010 through physical contact. Diffuser 1030 may electrically couple to spear 1010 via ionization of air in gap 1054 between diffuser 1030 and spear 1010. Diffuser 1030 electrically couples to a conductor of a filament (not shown), as discussed above.

Preferably, diffuser 1030 is placed as far away from spear 1010 as possible while still being positioned on forward portion 1042. For example, when diameter 1044 of body 1040 is about 0.213 inches, diffuser length 1050 is about 0.89 inches, diffuser diameter is about 0.015 inches, and a minimum separation 1054 of surfaces of spear 1010 and a diffuser 1030 is about 0.07 inches.

When electrode placement at the target includes piercing of target tissue by both spear 1010 and one or more of diffusers 1020 and 1030, target tissue is interposed between spear 1010 and a diffuser. Activation of spear 1010 involves a current path through target tissue. A current path may be formed from one or more diffusers and the return path through target tissue.

A diffuser may have a tip 1032 and a shaft 1031. The tip may be analogous in structure and function to the tip of a mechanical coupling structure or spear discussed above. The tip may be conductive. The diffuser may comprise an insulator that electrically insulates the diffuser (e.g., shaft) except for the tip. The operating point of the diffuser is thereby constrained to the tip, preferably a pointed portion of the tip for focusing electric field flux. Focusing may initially direct electric field flux away from spear 1010 to increase the likelihood that ionization and/or current paths will include target tissue.

The shaft of a diffuser may maintain a distance 1054 between the tip and other components of an electrode throughout launch and impact with target material or tissue. Maintaining may be accomplished by aligning a central axis of a diffuser (e.g., shaft) in the direction of flight.

In another implementation the shaft of a diffuser on impact with target material or tissue directs the tip away from other components of the electrode to increase a path or increase a quantity of paths of current through target tissue. For example, directing tip 1032 away from spear 1010 may be accomplished by initially aligning a central axis of diffuser 1030 (or shaft 1031) slightly away (not shown) from the direction of flight. In such an implementation, shaft 1031 may flex to avoid tearing target tissue.

Diffuser 1030 may pierce target material and/or tissue. When target material and/or tissue enters a gap between diffuser 1030 and spear 1010, the electrical relationship between diffuser 1030 and spear 1010 is changed. While target tissue is positioned between diffuser 1030 and spear 1010, the likelihood of current arcing from diffuser 1030 to spear 1010 may be decreased and a magnitude of current provided by a filament (not shown) through diffuser 1030 into target tissue may increase.

The structures discussed above as components of an electrode may be combined using conventional mechanical and electrical technologies in various implementations of the present invention. For example, a body and spear may be formed of one material as one structure to avoid the cost of assembling a spear with a body.

EXAMPLES OF THE INVENTION

First, a deployment unit provides a current through tissue of a target. The current inhibits voluntary movement by the target. The deployment unit includes a housing, at least one electrode, at least one filament, and a propellant. An end of the filament is mechanically coupled to the electrode. The electrode includes means for spreading the current.

In operation, the propellant propels the electrode away from the housing toward the target to extend the filament from the deployment unit toward the target. Structures of the electrode mechanically couple the electrode into the target. The filament conducts the current. Due to the position and orientation of the means for spreading the current, more of the current passes from the filament to a surface of tissue of the target than is conducted by the electrode into tissue of the target.

Second, a deployment unit provides a current from a signal generator through tissue of a target to inhibit voluntary movement by the target. The deployment unit includes a filament, a housing, an electrode, and a propellant. The filament conducts the current. The housing retains a first end of the filament. The electrode is initially in the housing. In operation, the propellant in the housing propels the electrode away from the housing to deploy the filament toward the target. The electrode comprises a body, and two structures. The body is mechanically coupled to the filament near a second end of the filament. The first structure, after deployment, mechanically couples the body to the target. The second structure, supported by the body, spreads the current from the filament to flow in part through the first structure and in balance through the second structure.

Third, a deployment unit provides a current through a target, the current for inhibiting voluntary movement by the target. The deployment unit includes at least one electrode and a propellant. The electrode includes a filament, means for mechanically coupling the electrode to the target, and means for focusing an electric field. A conductor of the filament is electrically isolated from the means for mechanically coupling the electrode to the target without an ionizing voltage between the conductor and the means for mechanically coupling. The means for focusing an electric field is positioned a length of a gap of air away from the means for mechanical coupling.

In operation, the propellant propels the electrode toward the target. The filament provides the current to the electrode. The electrode is capable of providing the current to target tissue via the gap and/or via the means for focusing.

Fourth, a deployment unit provides a current through a target, the current for inhibiting voluntary movement by the target. The deployment unit includes at least one electrode and a propellant. The electrode includes a filament that provides the current to the electrode, and further includes a mechanical coupling structure. The mechanical coupling structure is electrically isolated from the filament without an ionizing voltage between the mechanical coupling structure and the filament.

In operation, the propellant propels the electrode toward the target. The electrode provides the current to target tissue via a path from the spreading structure to the mechanical coupling structure and/or via the spreading structure.

Fifth, an electronic weapon provides a current through a target. The current inhibits voluntary movement by the target. The electronic weapon includes a launch device and a deployment unit that cooperate to launch at least one electrode toward the target. The launch device includes a signal generator for providing the current. The deployment unit includes a filament and the electrode. The filament electrically couples the signal generator to the electrode. The electrode includes a body and a tip. The body has a forward portion with reference to a direction of flight of the electrode toward the target. The tip extends forward of the forward portion. An end portion of the filament extends forward of the forward portion between the forward portion and the tip. The end portion provides the current through the target.

Sixth, a deployment unit provides a current through a target. The current inhibits voluntary movement by the target. The deployment unit includes an electrode and a means for propelling the electrode toward the target. The electrode includes a filament, a means for binding the filament to the electrode, a means for lodging the electrode into the target, and a means for spreading the current in tissue of the target. The filament conducts the current to the means for spreading. However, the means for binding is insulated from a conductor of the filament without ionization. Further, the means for lodging is also electrically insulated from the conductor of the filament without ionization.

In operation, the deployment unit receives operating current conducted to the means for spreading. The means for spreading supports a path by ionization to the means for lodging to provide at least a portion of the current.

Seventh, a deployment unit provides a current through a target for inhibiting voluntary movement by the target. The deployment unit includes an electrode and a propellant for propelling the electrode toward the target. The electrode includes a spear and a diffuser. The spear mechanically couples the electrode to the target. The diffuser is positioned a length of a gap of air away from the spear.

In operation, the diffuser provides the current through the target in accordance with a position of the spear and the diffuser relative to target tissue. The diffuser supports ionization of air in the gap when a lower resistance path for the current is not available.

Eighth, an electrode includes a spear and a diffuser. The electrode is for launching toward a provided target to provide a current through the target where the current inhibits voluntary movement by the target. The diffuser is positioned a length of a gap of air away from the spear. The diffuser provides the current through the target via at least one of the spear and the diffuser in accordance with a position of the spear, the diffuser, and the target tissue relative to each other. The diffuser supports ionization of air in the gap when a lower resistance path for the current is not available.

Nine, an electrode for launching toward a provided target provides a current from a signal generator through the target. The signal generator is not part of the electrode. The current inhibits voluntary movement by the target. The electrode includes a body, a spear, and a diffuser. The body includes a forward portion with reference to a direction of flight of the electrode toward the target. The spear is mechanically coupled to the forward portion of the body. The diffuser is mechanically coupled to the forward portion of the body and positioned a length of a gap of air away from the spear. The signal generator is electrically coupled to the diffuser.

In operation, to provide the current to the target, the diffuser is capable of electrically coupling to the spear via ionization of air in the gap, is capable of coupling to target tissue without ionization, and is capable of coupling to target tissue with ionization.

Tenth, a method is performed by a deployment unit for providing a current through a target. The current inhibits voluntary movement by the target. The method includes in any practical order: (a) propelling an electrode of the deployment unit toward a target; (b) positioning a diffuser and a spear of the electrode in or near target tissue; and (c) activating a forward portion of the spear via the diffuser to deliver the current.

Eleventh, a method is performed by a deployment unit for providing a current through a target. The current inhibits voluntary movement by the target. The method includes in any practical order: (a) propelling an electrode of the deployment unit toward a target to impact the target; (b) responsive to a force of impact, positioning a spear and a diffuser of the electrode relative to target tissue; (c) in accordance with positioning, providing a current through the target via any combination of the spear, the diffuser, a first gap of air between the spear and target tissue, a second gap of air between the spear and the diffuser, and a third gap of air between the diffuser and target tissue.

Twelfth, an electrode provides indicia of delivery of a current through a target. The current inhibits voluntary movement by the target. The electrode includes a body and a spear. The body includes a forward portion with reference to a direction of flight of the electrode toward the target. The spear mechanically couples to the body and extends forward of the forward portion of the body. An insulated wire mechanically couples the electrode to a source of the current. Local heating of the wire produces deformation of the wire. The wire is mechanically coupled to the body. An end portion of the wire extends forward of the forward portion of the body. An insulator of the wire concentrates an electric field of the current to ionize air in at least one of a first gap and a second gap. The first gap separates a conductor of the wire from the spear. The second gap separates the conductor from target tissue. Ionization of air in either gap, with resulting heat, provides indicia of delivery of the current comprising deformation of the wire.

The foregoing description discusses preferred embodiments of the present invention, which may be changed or modified without departing from the scope of the present invention as defined in the claims. Examples listed in parentheses may be used in the alternative or in any practical combination. As used in the specification and claims, the words 'comprising', 'including', and 'having' introduce an open ended statement of component structures and/or functions. In the specification and claims, the words 'a' and 'an' are used as indefinite articles meaning 'one or more'. While for the sake of clarity of description, several specific embodiments of the invention have been described, the scope of the invention is intended to be measured by the claims as set forth below.

What is claimed is:

1. An electrode, for providing a current from an electronic weapon through tissue of a human or animal target, the current for inhibiting voluntary movement by the target, the electrode comprising:

a. a body;

b. a shaft, supported by the body, that conducts the current; and c. a tip, supported by the shaft, that mechanically couples the electrode to clothing or tissue of the target; wherein d. the tip comprises insulative material.

2. The electrode of claim 1 wherein the electrode comprises one tip.

3. The electrode of claim 1 wherein, in at least one relative position of the electrode and tissue of the target when the tip is mechanically coupled to clothing or tissue of the target, more of the current flows into target tissue from the shaft than from the tip.

4. The electrode of claim 1 wherein the shaft comprises insulative material.

5. The electrode of claim 4 wherein the insulative material coats a portion of the shaft.

6. The electrode of claim 1 wherein the insulative material coats a portion of the tip.

7. A deployment unit for providing a current from a signal generator through tissue of a human or animal target, the current for inhibiting voluntary movement by the target, the deployment unit comprising:

a. a housing;

b. an interface that couples the housing to the signal generator, the interface for receiving the current;

c. a filament that conducts the current, the filament stored in the housing prior to deployment, the filament coupled to the interface for receiving the current;

d. an electrode comprising (1) a body;

(2) a shaft, supported by the body, that conducts the current; and (3) a tip, supported by the shaft, that mechanically couples the electrode to clothing or tissue of the target; wherein (4) the tip comprises insulative material.

8. The deployment unit of claim 7 the electrode comprises one tip.

9. The deployment unit of claim 7 wherein, in at least one relative position of the electrode and tissue of the target when the tip is mechanically coupled to clothing or tissue of the target, more of the current flows into target tissue from the shaft than from the tip.

10. The deployment unit of claim 7 wherein the shaft comprises insulative material.

11. The deployment unit of claim 10 wherein the insulative material coats a portion of the shaft.

12. The deployment unit of claim 7 wherein the insulative material coats a portion of the tip.

13. A method for conducting a current from an electronic weapon into tissue of a human or animal target, the method comprising:

a. propelling at least one wire-tethered electrode to impact the target to form a circuit for the current through tissue of the target; and b. after at least a tip of the electrode is in contact with tissue of the target, conducting more of the current into tissue of the target from a shaft of the electrode than from the tip of the electrode, wherein the current interferes with the target's voluntary use of its skeletal muscles.

14. The method of claim 13 wherein interfering comprises causing involuntary contraction of skeletal muscles.

15. The method of claim 13 wherein interfering comprises causing pain to the target to motivate the target to voluntarily stop moving.

* * * * *